United States Patent
Chen et al.

(10) Patent No.: US 10,471,001 B2
(45) Date of Patent: *Nov. 12, 2019

(54) SHORT DURATION DEPOT FORMULATIONS

(71) Applicant: Durect Corporation, Cupertino, CA (US)

(72) Inventors: Guohua Chen, Sunnyvale, CA (US); David T. Priebe, Bellevue, WA (US)

(73) Assignee: Durect Corporation, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,889

(22) Filed: Dec. 28, 2018

(65) Prior Publication Data

US 2019/0183791 A1    Jun. 20, 2019

Related U.S. Application Data

(60) Continuation of application No. 15/267,070, filed on Sep. 15, 2016, now Pat. No. 10,201,496, which is a continuation of application No. 11/278,472, filed on Apr. 3, 2006, now abandoned, which is a division of application No. 10/606,969, filed on Jun. 25, 2003, now abandoned.

(60) Provisional application No. 60/391,867, filed on Jun. 25, 2002.

(51) Int. Cl.
| | |
|---|---|
| A61K 9/00 | (2006.01) |
| A61K 47/10 | (2017.01) |
| A61K 47/14 | (2017.01) |
| A61K 9/06 | (2006.01) |
| A61K 31/445 | (2006.01) |
| A61K 38/27 | (2006.01) |
| A61K 47/34 | (2017.01) |

(52) U.S. Cl.
CPC .......... *A61K 9/0024* (2013.01); *A61K 9/0014* (2013.01); *A61K 9/0019* (2013.01); *A61K 9/06* (2013.01); *A61K 31/445* (2013.01); *A61K 38/27* (2013.01); *A61K 47/10* (2013.01); *A61K 47/14* (2013.01); *A61K 47/34* (2013.01)

(58) Field of Classification Search
None
See application file for complete search history.

(56) References Cited

U.S. PATENT DOCUMENTS

| | | |
|---|---|---|
| 2,931,802 A | 4/1960 | Touey et al. |
| 3,412,890 A | 11/1968 | Rich |
| 3,743,398 A | 7/1973 | Johnson et al. |
| 3,797,492 A | 3/1974 | Place |
| 3,828,389 A | 8/1974 | Heisler |
| 3,853,837 A | 12/1974 | Fujino et al. |
| 3,923,939 A | 12/1975 | Baker et al. |
| 3,987,790 A | 10/1976 | Eckenhoff et al. |
| 3,992,365 A | 11/1976 | Beddell et al. |
| 4,008,719 A | 2/1977 | Theeuwes et al. |
| 4,024,248 A | 5/1977 | Konig et al. |
| 4,079,038 A | 3/1978 | Choi et al. |
| 4,093,709 A | 6/1978 | Choi et al. |
| 4,100,274 A | 7/1978 | Dutta et al. |
| 4,131,648 A | 12/1978 | Choi et al. |
| 4,138,344 A | 6/1979 | Choi et al. |
| 4,180,646 A | 12/1979 | Choi et al. |
| 4,304,767 A | 8/1981 | Heller et al. |
| 4,322,323 A | 3/1982 | Capoza |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,443,340 A | 4/1984 | May et al. |
| 4,487,603 A | 12/1984 | Harris |
| 4,530,840 A | 7/1985 | Tice et al. |
| 4,549,010 A | 10/1985 | Sparer et al. |
| 4,586,559 A | 5/1986 | Govaerts et al. |
| 4,622,219 A | 11/1986 | Haynes |
| 4,623,588 A | 11/1986 | Nuwayser et al. |
| 4,668,506 A | 5/1987 | Bawa |
| 4,692,147 A | 9/1987 | Duggan |
| 4,708,861 A | 11/1987 | Popescu et al. |
| 4,711,782 A | 12/1987 | Okada et al. |
| 4,713,244 A | 12/1987 | Bawa et al. |
| 4,725,442 A | 2/1988 | Haynes |
| 4,725,852 A | 2/1988 | Gamblin et al. |

(Continued)

FOREIGN PATENT DOCUMENTS

| | | |
|---|---|---|
| AU | 8374575 | 8/1975 |
| CA | 2222567 | 12/1996 |

(Continued)

OTHER PUBLICATIONS

U.S. Appl. No. 15/870,745, filed Jan. 12, 2018, Verity.
U.S. Appl. No. 16/281,026, filed Feb. 20, 2019, Verity.
U.S. Appl. No. 16/297,509, filed Mar. 8, 2019, Chen et al.
"3M DDS Announces Development of New HFA-Compatible Excipients: Novel Oligomeric Acids as MDI Suspension Aids and Solubilizers," 3M Delivery Newsletter, 3M Drug Delivery Systems, vol. 15, Jun. 2000.
"New Drugs/Programs", Current Drug Discovery, Nov. 2004 pp. 7-10.

(Continued)

*Primary Examiner* — Jake M Vu

(57) ABSTRACT

Methods and compositions for systemically or locally administering by implantation a beneficial agent to a subject are described, and include, for example, depot gel compositions that can be injected into a desired location and which can provide controlled release of a beneficial agent over a short duration of time. The compositions include a low molecular weight biocompatible polymer, a biocompatible solvent having low water miscibility that forms a viscous gel with the polymer and limits water uptake by the implant, and a beneficial agent.

42 Claims, 13 Drawing Sheets

(56) References Cited

U.S. PATENT DOCUMENTS

| | | |
|---|---|---|
| 4,745,160 A | 5/1988 | Churchill et al. |
| 4,767,628 A | 8/1988 | Hutchinson |
| 4,780,319 A | 10/1988 | Zentner et al. |
| 4,795,641 A | 1/1989 | Kashdan |
| 4,834,984 A | 5/1989 | Goldie et al. |
| 4,844,909 A | 7/1989 | Goldie et al. |
| 4,853,218 A | 8/1989 | Yim et al. |
| 4,861,598 A | 8/1989 | Oshlack |
| 4,865,845 A | 9/1989 | Eckenhoff et al. |
| 4,866,050 A | 9/1989 | Ben-Amoz |
| 4,891,225 A | 1/1990 | Langer et al. |
| 4,906,474 A | 3/1990 | Langer et al. |
| 4,931,279 A | 6/1990 | Bawa et al. |
| 4,938,763 A | 7/1990 | Dunn et al. |
| 4,946,931 A | 8/1990 | Heller et al. |
| 4,957,744 A | 9/1990 | della Valle et al. |
| 4,957,998 A | 9/1990 | Heller et al. |
| 4,970,075 A | 11/1990 | Oshlack |
| 4,985,404 A | 1/1991 | Mitchell et al. |
| 4,990,341 A | 2/1991 | Goldie et al. |
| 5,019,400 A | 5/1991 | Gombotz et al. |
| 5,057,318 A | 10/1991 | Magruder et al. |
| 5,059,423 A | 10/1991 | Magruder et al. |
| 5,061,492 A | 10/1991 | Okada et al. |
| 5,077,033 A | 12/1991 | Viegas et al. |
| 5,085,866 A | 2/1992 | Cowsar et al. |
| 5,112,614 A | 5/1992 | Magruder et al. |
| 5,137,727 A | 8/1992 | Eckenhoff et al. |
| 5,149,543 A | 9/1992 | Cohen et al. |
| 5,151,093 A | 9/1992 | Theeuwes et al. |
| 5,181,914 A | 1/1993 | Zook |
| 5,188,837 A | 2/1993 | Domb |
| 5,209,746 A | 5/1993 | Balaban et al. |
| 5,211,951 A | 5/1993 | Sparer et al. |
| 5,234,692 A | 8/1993 | Magruder et al. |
| 5,234,693 A | 8/1993 | Magruder et al. |
| 5,242,910 A | 9/1993 | Damnj |
| 5,252,318 A | 10/1993 | Joshi et al. |
| 5,266,331 A | 11/1993 | Oshlack et al. |
| 5,278,201 A | 1/1994 | Dunn et al. |
| 5,278,202 A | 1/1994 | Dunn et al. |
| 5,279,608 A | 1/1994 | Cheikh |
| 5,286,496 A | 2/1994 | Stapler et al. |
| 5,308,348 A | 5/1994 | Bakaban et al. |
| 5,310,865 A | 5/1994 | Enomoto et al. |
| 5,324,519 A | 6/1994 | Dunn et al. |
| 5,324,520 A | 6/1994 | Dunn et al. |
| 5,330,452 A | 7/1994 | Zook |
| 5,330,835 A | 7/1994 | Kikuchi et al. |
| 5,300,295 A | 8/1994 | Viegas et al. |
| 5,336,057 A | 8/1994 | Fukuda et al. |
| 5,340,572 A | 8/1994 | Patel et al. |
| 5,340,614 A | 8/1994 | Perman et al. |
| 5,340,849 A | 8/1994 | Dunn et al. |
| 5,342,627 A | 8/1994 | Chopra et al. |
| 5,350,741 A | 9/1994 | Takada |
| 5,352,662 A | 10/1994 | Brooks et al. |
| 5,356,635 A | 10/1994 | Raman et al. |
| 5,382,424 A | 1/1995 | Stapler et al. |
| 5,391,381 A | 2/1995 | Wong et al. |
| 5,399,363 A | 3/1995 | Liversidge et al. |
| 5,415,866 A | 5/1995 | Zook |
| 5,441,732 A | 8/1995 | Hoeg et al. |
| 5,447,725 A | 9/1995 | Damani et al. |
| 5,478,577 A | 12/1995 | Sackler et al. |
| 5,487,898 A | 1/1996 | Lu et al. |
| 5,492,253 A | 2/1996 | Proshan |
| 5,540,912 A | 7/1996 | Roorda et al. |
| 5,545,408 A | 8/1996 | Trigg et al. |
| 5,549,912 A | 8/1996 | Oshlack et al. |
| 5,556,905 A | 9/1996 | Frappier et al. |
| 5,569,450 A | 10/1996 | Duan et al. |
| 5,571,525 A | 11/1996 | Roorda et al. |
| 5,599,534 A | 2/1997 | Himmelstein et al. |
| 5,599,552 A | 2/1997 | Dunn et al. |
| 5,607,686 A | 3/1997 | Totakura et al. |
| 5,610,184 A | 3/1997 | Shahinian, Jr. |
| 5,614,206 A | 3/1997 | Randolph et al. |
| 5,618,563 A | 4/1997 | Berde et al. |
| 5,620,700 A | 4/1997 | Berggen et al. |
| 5,632,727 A | 5/1997 | Tipton et al. |
| 5,633,000 A | 5/1997 | Grossman et al. |
| 5,651,986 A | 7/1997 | Brem et al. |
| 5,654,010 A | 8/1997 | Johnson et al. |
| 5,656,295 A | 8/1997 | Oshlack et al. |
| 5,656,297 A | 8/1997 | Bernstein et al. |
| 5,660,817 A | 8/1997 | Masterman et al. |
| 5,672,360 A | 9/1997 | Sackler et al. |
| 5,681,873 A | 10/1997 | Norton et al. |
| 5,700,485 A | 12/1997 | Berde et al. |
| 5,702,716 A | 12/1997 | Dunn et al. |
| 5,707,647 A | 1/1998 | Dunn et al. |
| 5,707,664 A | 1/1998 | Illum |
| 5,708,011 A | 1/1998 | Bardsley et al. |
| 5,717,030 A | 2/1998 | Dunn et al. |
| 5,725,491 A | 3/1998 | Tipton et al. |
| 5,725,841 A | 3/1998 | Dunn et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,747,051 A | 5/1998 | Granger et al. |
| 5,747,058 A | 5/1998 | Tipton et al. |
| 5,747,060 A | 5/1998 | Sackler et al. |
| 5,750,100 A | 5/1998 | Yamagata et al. |
| 5,759,563 A | 6/1998 | Yewey et al. |
| 5,760,077 A | 6/1998 | Shahinian, Jr. |
| 5,766,637 A | 6/1998 | Shine et al. |
| 5,777,124 A | 7/1998 | Zavareh et al. |
| 5,780,044 A | 7/1998 | Yewey et al. |
| 5,783,205 A | 7/1998 | Berggren et al. |
| 5,786,484 A | 7/1998 | Dyer et al. |
| 5,787,175 A | 7/1998 | Carter |
| 5,792,469 A | 8/1998 | Tipton et al. |
| 5,804,212 A | 9/1998 | Illum |
| 5,837,228 A | 11/1998 | Shih et al. |
| 5,840,329 A | 11/1998 | Bai |
| 5,849,763 A | 12/1998 | Bardsley et al. |
| 5,879,705 A | 3/1999 | Heafield et al. |
| 5,910,502 A | 6/1999 | Gennery |
| 5,919,473 A | 7/1999 | Elkhoury |
| 5,919,835 A | 7/1999 | Domb et al. |
| 5,922,340 A | 7/1999 | Berde et al. |
| 5,932,597 A | 8/1999 | Brown |
| 5,939,453 A | 8/1999 | Heller et al. |
| 5,942,241 A | 8/1999 | Chasin et al. |
| 5,942,253 A | 8/1999 | Gombotz et al. |
| 5,945,115 A | 8/1999 | Dunn et al. |
| 5,958,443 A | 9/1999 | Viegas et al. |
| 5,968,542 A | 10/1999 | Tipton |
| 5,968,543 A | 10/1999 | Heller et al. |
| 5,972,326 A | 10/1999 | Galin et al. |
| 5,972,366 A | 10/1999 | Haynes et al. |
| 5,985,305 A | 11/1999 | Peery et al. |
| 5,990,194 A | 11/1999 | Dunn et al. |
| 5,993,856 A | 11/1999 | Ragavan et al. |
| 5,994,548 A | 11/1999 | Langston et al. |
| 6,004,295 A | 12/1999 | Langer et al. |
| 6,007,845 A | 12/1999 | Domb et al. |
| 6,008,355 A | 12/1999 | Huang et al. |
| 6,042,811 A | 3/2000 | Duan et al. |
| 6,046,187 A | 4/2000 | Berde et al. |
| 6,050,986 A | 4/2000 | Hektner |
| 6,051,558 A | 4/2000 | Burns et al. |
| 6,086,909 A | 7/2000 | Harrison et al. |
| 6,102,235 A | 8/2000 | Stern et al. |
| 6,103,266 A | 8/2000 | Tapolski et al. |
| 6,106,301 A | 8/2000 | Merril |
| 6,117,425 A | 9/2000 | McPhee et al. |
| 6,119,890 A | 9/2000 | Kawamata |
| 6,120,789 A | 9/2000 | Dunn |
| 6,120,804 A | 9/2000 | Drizen et al. |
| 6,126,919 A | 10/2000 | Stefely et al. |

(56) References Cited

U.S. PATENT DOCUMENTS

| | | |
|---|---|---|
| 6,129,933 A | 10/2000 | Oshlack et al. |
| 6,130,200 A | 10/2000 | Brodbeck et al. |
| 6,132,766 A | 10/2000 | Sankaram et al. |
| 6,136,334 A | 10/2000 | Viegas et al. |
| 6,143,314 A | 11/2000 | Chandeashekar et al. |
| 6,143,322 A | 11/2000 | Sackler et al. |
| 6,193,991 B1 | 2/2001 | Shukla |
| 6,193,994 B1 | 2/2001 | Lee et al. |
| 6,197,327 B1 | 3/2001 | Harrison et al. |
| 6,203,813 B1 | 3/2001 | Gooberman |
| 6,214,387 B1 | 4/2001 | Berde et al. |
| 6,217,911 B1 | 4/2001 | Vaung et al. |
| 6,238,702 B1 | 5/2001 | Berde et al. |
| 6,245,351 B1 | 6/2001 | Nara et al. |
| 6,248,345 B1 | 6/2001 | Goldenheim et al. |
| 6,255,502 B1 | 7/2001 | Penkler et al. |
| 6,261,547 B1 | 7/2001 | Bawa et al. |
| 6,291,013 B1 | 9/2001 | Gibson et al. |
| 6,309,375 B1 | 10/2001 | Glines et al. |
| 6,312,717 B1 | 11/2001 | Molinoff et al. |
| 6,322,548 B1 | 11/2001 | Payne et al. |
| 6,331,311 B1 | 12/2001 | Brodbeck et al. |
| 6,352,667 B1 | 3/2002 | English |
| 6,355,273 B1 | 3/2002 | Carli et al. |
| 6,372,245 B1 | 4/2002 | Bowman et al. |
| 6,375,659 B1 | 4/2002 | Erbe et al. |
| 6,384,227 B2 | 5/2002 | Dyer et al. |
| 6,395,293 B2 | 5/2002 | Polson et al. |
| 6,403,057 B1 | 6/2002 | Schneider et al. |
| 6,403,609 B1 | 6/2002 | Asgharian |
| 6,413,536 B1 | 7/2002 | Gibson et al. |
| 6,417,201 B1 | 7/2002 | Bardsley et al. |
| 6,423,818 B1 | 7/2002 | Matsuda et al. |
| 6,426,339 B1 | 7/2002 | Berde et al. |
| 6,432,415 B1 | 8/2002 | Osborne et al. |
| 6,440,493 B1 | 8/2002 | Gibson et al. |
| 6,451,346 B1 | 9/2002 | Shah |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,514,516 B1 | 2/2003 | Chasin et al. |
| 6,521,259 B1 | 2/2003 | Chasin et al. |
| 6,524,606 B1 | 2/2003 | Ng et al. |
| 6,524,607 B1 | 2/2003 | Goldenheim et al. |
| 6,543,081 B1 | 3/2003 | Goldenheim et al. |
| 6,590,059 B2 | 7/2003 | Ng et al. |
| 6,613,335 B1 | 9/2003 | Ruelle |
| 6,673,767 B1 | 1/2004 | Brodbeck et al. |
| 6,699,908 B2 | 3/2004 | Sackler et al. |
| 6,733,783 B2 | 5/2004 | Oshlack et al. |
| 6,863,782 B2 | 3/2005 | Newsome et al. |
| 6,921,541 B2 | 7/2005 | Chasin et al. |
| 6,992,065 B2 | 1/2006 | Okumu |
| 7,053,209 B1 | 5/2006 | Gibson et al. |
| 7,128,927 B1 | 10/2006 | Dunn |
| 7,368,126 B2 | 5/2008 | Chen et al. |
| 7,829,109 B2 | 11/2010 | Chen et al. |
| 7,833,543 B2 | 11/2010 | Gibson et al. |
| 8,110,209 B2 | 2/2012 | Prestrelski et al. |
| 8,153,149 B2 | 4/2012 | Verity |
| 8,153,661 B2 | 4/2012 | Verity |
| 8,252,303 B2 | 8/2012 | Chen et al. |
| 8,252,304 B2 | 8/2012 | Ng et al. |
| 8,278,330 B2 | 10/2012 | Chen et al. |
| 8,501,215 B2 | 8/2013 | Chen et al. |
| 8,753,665 B2 | 6/2014 | Verity |
| 8,834,921 B2 | 9/2014 | Kim et al. |
| 8,846,072 B2 | 9/2014 | Verity |
| 9,192,575 B2 | 11/2015 | Kim et al. |
| 9,205,052 B2 | 12/2015 | Kim et al. |
| 9,585,838 B2 | 3/2017 | Hartounian et al. |
| 10,201,496 B2 * | 2/2019 | Chen .................. A61K 9/0014 |
| 2001/0000522 A1 | 4/2001 | Dyer et al. |
| 2001/0004644 A1 | 6/2001 | Levin |
| 2001/0013518 A1 | 8/2001 | Lallement et al. |
| 2001/0029257 A1 | 10/2001 | Murdock et al. |
| 2001/0046518 A1 | 11/2001 | Sawhney |
| 2001/0055607 A1 | 12/2001 | Levin |
| 2002/0001608 A1 | 1/2002 | Polson et al. |
| 2002/0001631 A1 | 1/2002 | Okumu |
| 2002/0004063 A1 | 1/2002 | Zhang |
| 2002/0010150 A1 | 1/2002 | Cortese et al. |
| 2002/0016338 A1 | 2/2002 | Mather et al. |
| 2002/0028181 A1 | 3/2002 | Miller et al. |
| 2002/0028243 A1 | 3/2002 | Masters |
| 2002/0037104 A1 | 3/2002 | Myers et al. |
| 2002/0037300 A1 | 3/2002 | Ng et al. |
| 2002/0037358 A1 | 3/2002 | Barry et al. |
| 2002/0141966 A1 | 3/2002 | Dang |
| 2002/0039594 A1 | 4/2002 | Unger |
| 2002/0045668 A1 | 4/2002 | Dang et al. |
| 2002/0061326 A1 | 5/2002 | Li et al. |
| 2002/0086971 A1 | 7/2002 | Pham |
| 2002/0114835 A1 | 8/2002 | Sackler et al. |
| 2002/0054915 A1 | 9/2002 | Goldenheim et al. |
| 2002/0168336 A1 | 11/2002 | Ng et al. |
| 2002/0176844 A1 | 11/2002 | Ng et al. |
| 2003/0045454 A1 | 3/2003 | Okumu et al. |
| 2003/0152630 A1 | 8/2003 | Ng et al. |
| 2003/0152634 A1 | 8/2003 | Bodmeier |
| 2003/0152637 A1 | 8/2003 | Chasin et al. |
| 2003/0180364 A1 | 9/2003 | Chen et al. |
| 2003/0185873 A1 | 10/2003 | Chasin et al. |
| 2003/0170289 A1 | 11/2003 | Chen et al. |
| 2004/0001889 A1 | 1/2004 | Chen et al. |
| 2004/0018238 A1 | 1/2004 | Shukla |
| 2004/0024021 A1 | 2/2004 | Sudo et al. |
| 2004/0037885 A1 | 2/2004 | Seo et al. |
| 2004/0052336 A1 | 3/2004 | Langlet et al. |
| 2004/0106987 A1 | 3/2004 | Palasis et al. |
| 2004/0022859 A1 | 5/2004 | Chen et al. |
| 2004/0024069 A1 | 5/2004 | Chen et al. |
| 2004/0101557 A1 | 5/2004 | Gibson et al. |
| 2004/0151753 A1 | 5/2004 | Chen et al. |
| 2004/0151774 A1 | 5/2004 | Pauletti et al. |
| 2004/0109893 A1 | 6/2004 | Chen et al. |
| 2004/0138237 A1 | 7/2004 | Shah |
| 2004/0146562 A1 | 7/2004 | Shah |
| 2004/0224903 A1 | 11/2004 | Berry et al. |
| 2005/0042194 A1 | 2/2005 | Ng et al. |
| 2005/0106304 A1 | 5/2005 | Cook et al. |
| 2005/0171052 A1 | 8/2005 | Cook et al. |
| 2005/0232876 A1 | 10/2005 | Minga et al. |
| 2005/0244489 A1 | 11/2005 | Paris |
| 2005/0266087 A1 | 12/2005 | Junnarkar et al. |
| 2006/0034926 A1 | 2/2006 | Fraatz et al. |
| 2006/0058401 A1 | 3/2006 | Ishikawa et al. |
| 2006/0155101 A1 | 7/2006 | Heller et al. |
| 2006/0165800 A1 | 7/2006 | Chen et al. |
| 2006/0121085 A1 | 8/2006 | Warren et al. |
| 2006/0210599 A1 | 9/2006 | Gibson et al. |
| 2008/0023261 A1 | 1/2008 | Kaneko et al. |
| 2008/0145419 A1 | 6/2008 | Gibson et al. |
| 2008/0152708 A1 | 6/2008 | Gibson et al. |
| 2008/0167630 A1 | 7/2008 | Verity |
| 2008/0206321 A1 | 8/2008 | Yum et al. |
| 2009/0023689 A1 | 1/2009 | Yum et al. |
| 2009/0023690 A1 | 1/2009 | Yum et al. |
| 2009/0036490 A1 | 2/2009 | Verity |
| 2010/0160375 A1 | 6/2010 | King |
| 2011/0009451 A1 | 1/2011 | Verity |
| 2011/0046181 A1 | 2/2011 | Chen et al. |
| 2013/0289069 A1 | 10/2013 | Verity |
| 2015/0111924 A1 | 4/2015 | Verity |
| 2016/0235726 A1 | 8/2016 | Verity |
| 2017/0087086 A1 | 3/2017 | Chen et al. |
| 2017/0216267 A1 | 8/2017 | Verity |
| 2018/0256553 A1 | 9/2018 | Verity |

FOREIGN PATENT DOCUMENTS

| | | |
|---|---|---|
| CA | 2379436 | 10/2002 |
| DE | 1569231 | 8/1969 |
| DE | 2213717 | 11/1972 |

(56) References Cited

FOREIGN PATENT DOCUMENTS

| | | |
|---|---|---|
| DE | 2321174 | 11/1973 |
| DE | 2438352 | 2/1976 |
| DE | 2720245 | 11/1977 |
| DE | 19714765 | 10/1998 |
| EP | 0244118 | 11/1987 |
| EP | 0290983 | 11/1988 |
| EP | 0535899 | 4/1993 |
| EP | 0537559 | 4/1993 |
| EP | 0539559 | 5/1993 |
| EP | 0539751 | 5/1993 |
| EP | 0621042 | 10/1994 |
| EP | 0635531 | 1/1995 |
| EP | 0640336 | 3/1995 |
| EP | 0711548 | 5/1996 |
| EP | 0773034 | 5/1997 |
| EP | 0795329 | 9/1997 |
| EP | 0999825 | 5/2000 |
| EP | 1010436 | 6/2000 |
| EP | 0782569 | 3/2002 |
| EP | 0862416 | 9/2002 |
| EP | 0804417 | 6/2003 |
| EP | 0788480 | 7/2003 |
| EP | 0788481 | 8/2003 |
| EP | 1348427 | 10/2003 |
| EP | 1032390 | 11/2003 |
| EP | 0778768 | 5/2004 |
| EP | 1515697 | 3/2005 |
| EP | 1548093 | 6/2005 |
| EP | 1100460 | 4/2008 |
| EP | 2238478 | 10/2010 |
| EP | 1809329 | 12/2011 |
| GB | 1088992 | 10/1967 |
| GB | 1218430 | 1/1971 |
| GB | 2238478 | 6/1991 |
| JP | S 59210024 | 11/1984 |
| JP | 62000419 | 1/1987 |
| JP | H 0296516 | 4/1990 |
| JP | 5194273 | 8/1993 |
| JP | H 0753356 | 2/1995 |
| JP | H 7112940 | 5/1995 |
| JP | H 7115901 | 5/1995 |
| JP | H 7124196 | 5/1995 |
| JP | 8501064 | 2/1996 |
| JP | 9502181 | 3/1997 |
| JP | 2001509146 | 7/2001 |
| JP | 2002512597 | 4/2002 |
| JP | 2004536036 | 12/2004 |
| JP | 2005514349 | 5/2005 |
| JP | 2005519873 | 7/2005 |
| JP | 2008513467 | 3/2006 |
| JP | 2008512597 | 4/2008 |
| NZ | 533435 | 10/2007 |
| NZ | 533436 | 10/2007 |
| NZ | 537955 | 10/2007 |
| WO | WO 1990003768 | 4/1990 |
| WO | WO 1990003809 | 4/1990 |
| WO | WO 1991017900 | 11/1991 |
| WO | WO 1991018016 | 11/1991 |
| WO | WO 1992011843 | 7/1992 |
| WO | WO 1993003751 | 3/1993 |
| WO | WO 1993007833 | 4/1993 |
| WO | WO 1993020134 | 10/1993 |
| WO | WO 1993024150 | 12/1993 |
| WO | WO 1994005226 | 3/1994 |
| WO | WO 1994014416 | 7/1994 |
| WO | WO 1994014417 | 7/1994 |
| WO | WO 1994015587 | 7/1994 |
| WO | WO 1994028935 | 12/1994 |
| WO | WO 1995009613 | 4/1995 |
| WO | WO 1995001379 | 5/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996021427 | 7/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 1999047073 | 9/1999 |
| WO | WO 1999062983 | 9/1999 |
| WO | WO 2000000120 | 1/2000 |
| WO | WO 2000074650 | 12/2000 |
| WO | WO 2000078335 | 12/2000 |
| WO | WO 2001003670 | 1/2001 |
| WO | WO 2001015734 | 3/2001 |
| WO | WO 2001051024 | 7/2001 |
| WO | WO 2001076599 | 10/2001 |
| WO | WO 2001085139 | 11/2001 |
| WO | WO 2002000137 | 1/2002 |
| WO | WO 2002001608 | 1/2002 |
| WO | WO 2002010436 | 2/2002 |
| WO | WO 1992007555 | 5/2002 |
| WO | WO 2002038185 | 5/2002 |
| WO | WO 2002053187 | 7/2002 |
| WO | WO 2002058670 | 8/2002 |
| WO | WO 2002067991 | 9/2002 |
| WO | WO 2003000282 | 1/2003 |
| WO | WO 2003041684 | 5/2003 |
| WO | WO 2003041685 | 5/2003 |
| WO | WO 2003041757 | 5/2003 |
| WO | WO 2003059320 | 7/2003 |
| WO | WO 2003082188 | 10/2003 |
| WO | WO 2003086368 | 10/2003 |
| WO | WO 2003101358 | 12/2003 |
| WO | WO 2004000269 | 12/2003 |
| WO | WO 2004011032 | 2/2004 |
| WO | WO 2004012703 | 2/2004 |
| WO | WO 2004014466 | 2/2004 |
| WO | WO 2004037224 | 5/2004 |
| WO | WO 2004037289 | 5/2004 |
| WO | WO 2004043432 | 5/2004 |
| WO | WO 2004052336 | 6/2004 |
| WO | WO 2004056338 | 7/2004 |
| WO | WO 2004082658 | 9/2004 |
| WO | WO 2004101557 | 11/2004 |
| WO | WO 2004108111 | 12/2004 |
| WO | WO 2005009408 | 2/2005 |
| WO | WO 2005048744 | 6/2005 |
| WO | WO 2005105031 | 11/2005 |
| WO | WO 2005115333 | 12/2005 |
| WO | WO 2006033948 | 3/2006 |
| WO | WO 2006084139 | 8/2006 |
| WO | WO 2006084141 | 8/2006 |
| WO | WO 2008023261 | 2/2008 |

OTHER PUBLICATIONS

Adams Eg, et al. "A comparison of the abuse liability of tramadol, NSAIDS, and hydrocodone in patients with chronic pain." Journal of Pain and Symptom Management. 3 1(5), 465-476 2006.

Ahuja et al. (1995) "Intra-Articular Morphine Versus Bupivacaine for Postoperative Analgesia Following Knee Arthroscopy" *The Knee* 2(4):227-231.

Ajayaghosh, A., et al., "Solid-Phase Synthesis of N-Methyl and N-Ethylamides of Peptides Using Photolytically Detachable ((3-Nitro-4-((alkylamino)methyl) benzamido)methyl)polystrene Resin," J. Org. Chem., 55:2826 (1990).

Allahham A, et al. "Flow and injection characteristics of pharmaceutical parenteral formulations using a micro-capillary rheometer". Int J Pharm. 2004;270(1-2): 139-48.

(56) References Cited

OTHER PUBLICATIONS

Ansel, H.C. et al., Pharmaceutical Dosage Forms and Drug Delivery System, sixth ed., (1995).
Barr, J., et al., Post surgical pain management with poly(ortho esters), Adv. Drug Del. Rev., 54 (2002) 1041-1048.
Barb, R. et al., "Evaluation of the Saber Delivery System for the Controlled Release of Deslorelin: Effect of Dose in Estrogen Primed Ovarectomized Gilts," Proceed. Int'l Symp. Control. Rel. Bioact. Mater., 26 (1999).
Bartfield et al. (1998) "Randomized Trial of Diphenhydramine Versus Benzyl Alcohol with Epinephrine as an Alternative to Lidocaine Local Anesthesia" Ann Emerg Med 32(6):650-654.
Bartfield et al. (2001) "Benzyl Alcohol with Epinephrine as an Alternative to Lidocaine With Epinephrine" J Emerg Med 21(4):375-379.
Becker, S.E., et al. "Effects of Gonadotropin-Releasing Hormone Infused in a Pulsatile or Continuous Fashion on Serum Gonadotropin Concentrations and Ovulation in the Mare," J. Anim. Sci. (1992) 70:1208-1215.
Bekersky I, et al. "Effect of low- and high-fat meals on tacrolimus absorption following 5 mg single oral doses to healthy human subjects." J Clin Pharmacol 2001 ; 4 1 (2): 176-82.
Betschart, R., et al., "Evaluation of the Saber™ Delivery System for the Controlled Release of the GnRH Analogue Deslorelin for Advancing Ovulation in Mares: Effect of Gamma Radiation," Proceed. Int'l Symp. Control. Rel. Bioact. Mater. 25 (1998) Controlled Release Society, Inc. pp. 655-656.
Blanco, M.D. et al. "Bupivacaine-loaded comatrix formed by alumin microspheres included in a poly(lactide-coglycolide) film: in vivo biocompatibility and drug release studies," Biomaterials, vol. 20, pp. 1919-1924, 1999.
Brevard J, et al. "Pain and opioid abuse in a population of substance abuse patients: data from the NAVIPPRO system." Conference paper presented at the 42nd American Pain Society (APS) Annual Scientific Meeting, Washington D.C., 2007.
Buhler, K. "GnRH Agonists and Safety" in GnRH Analogues the State of the Art 1993, A Summary of the 3rd International Symposium on GnRH Analogues in Cancer and Human Reproduction, Geneva, Feb. 1993.
Burns, P. et al., "Pharmacodynamic Evaluation of the Saber.TM. Delivery System for the Controlled Release of the GnRH Analogue Deslorelin Acetate for Advancing Ovulation in Cyclic Mares," Proceed. Int'l. Symp. Control. Rel. Bioact. Mater., 24 (1997), Controlled Release Society, Inc.
Castillo, J. et al., Glucocorticoids Prolong Rat Sciatic Nerve Blockade in Vivo from Bupivacaine Microspheres, Anesthesiology, 85, 1157-1166, 1996.
Cellulose Acetate Butyrate. In: European pharmacopoeia. 4 edn. Strasbourg Cedex, France: Council of Europe; 2001; p. 853-4.
Chia, H., et al., "Auto-Catalyzed poly(ortho ester) microspheres: a study of their erosion and drug release mechanism", J. Control. Rel. 75 (2001) 11-25.
Cleland, J.L. "Injectable Gels for Local and Systemic Delivery of Proteins," Proceed. Int'l. Symp. Control. Rel. Bioact. Mater., vol. 28, 2001.
Coy, et al., "Solid Phase Synthesis of Lutcinizing Hormone-Releasing Hormone and Its Analogs," Methods Enzymol. 37, 416 (1975).
Deng, J.; Li, L.; et al., "In vitro characterization of polyorthoester microparticles containing bupivacaine", Pharmaceutical Development and Technology, vol. 8, No. 1, pp. 31-38, 2003.
Desai, Neil P., et al. "Surface Modifications of Polymeric Biomaterials for Reduced Thrombogenicity," Polymeric Materials Science and Engineering, vol. 62, 1990 by ACS.
Dodson, K.M., et al. "Oral Controlled Release of Antiretrovirals Using the SABER Delivery System Incorporated into Soft Gelatin Capsules", AAPS Meeting, 1999, New Orleans, LA.
Duan, D. et al., "Novel Dispersing Aids for Hydrofluoroalkane-Based Metered Dose Inhalers," 1998 Conference of the American Association of Pharmaceutical Scientists, California, Nov. 1998.
Duan, D. et al., "Oligomeric Lactic Acids as Solubilizing Aids for HFA-Based Metered Dose Inhalers," 1998 Conference of the American Association of Pharmaceutical Scientists, San Francisco, California, Nov. 1998.
Dunbar Sa, Katz NP "Chronic opioid therapy for nonmalignant pain in patients with a history of substance abuse: report of 20 cases." Journal of Pain and Symptom Management. 1 1 (3), 163-1 7 1. 1996.
Duenas, E. et al. "Sustained Delivery of rhVEGF from a Novel Injectable Liquid, Plad" Proceed. Int'l. Symp. Control. Rel. Bioact. Mater., vol. 28, 2001.
Ekelund, A., et al., "Treatment of Postoperative Pain in Shoulder Surgery with SABER-Bupivacaine" Poster, Meeting: American Society of Regional Anesthesia and Pain Medicine (ASRA) Apr. 3-6, 2014.
Einmahl, S., et al., "Therapeutic applications of viscous and injectable poly(ortho esters)", Adv. Drug Del. Rev 53 (2001) 45-73.
Ellis, D., et al., "Treatment of Postoperative Pain in Shoulder Surgery with SABER-Bupivacaine," Poster, American Pain Society 32nd Annual Scientific Meeting, New Orleans, LA May 8, 2013.
English translation of Office Action, dated Oct. 29, 2009, from Japanese Application No. 516150/04, which is a family member of the present annlication.
English translation of Office Action, dated Jan. 12, 2010, from Japanese Application No. 504650/05, which is a family member of the present annlication.
Fitzgerald, B.P, et al., (1993) "Effect of Constant Administration of a Gonadotropin-Releasing Hormone Agonist on Reproductive Activity in Mares: Preliminary Evidence on Suppression of Ovulation During the Breeding Season," Am. J. Vet. Res., 54:10 1746-1751.
Fleury, J., et al., "Evaluation of the Saber.TM. Delivery System for the Controlled Release of the Deslorelin for Advancing Ovulation in the Mare: Effects of Formulation & Dose," Proceed. Int'l. Symp. Control. Rel. Bioact. Mater. 25 (1998) Controlled Release Society, Inc. pp. 657-658.
Gan, T., et al., "The Cardiac Safety of SABER-Bupivacaine in Patients Undergoing Abdominal Surgery: An assessment of Holter Monitoring Data from the BESST Trial", Poster & Abstract, International Anesthesia Research Society Annual Meeting, Fairmont Queen Elizabeth, Montreal, Canada, May 17-20, 2014.
Gan, T., et al., "SABER-Bupivacaine Reduced Pain Intensity for 72 Hours Following Abdominal Surgery Relative to Bupivacaine-HC1" Abstract, American Society of Anesthesiologists, 2014.
Gan, T., et al., "Treatment of Postoperative Pain in Major AbdominalSurgery with SABER-Bupivacaine: Results of the BESST Trial", AmericanSociety of Regional Anesthesia and Pain Medicine (ASRA) Apr. 3-6, 2014.
Garry, M.G. et al. "Evaluation of the efficiency of a bioerodible bupivacaine polymer system on antinociception and inflammatory mediator release," Pain, vol. 82, pp. 49-55, 1999.
Gilderman L., et al. "Remoxy™: A New Opioid Drug With Effective Analgesia and Abuse-Resistance." American Pain Society Annual Meeting, San Antonio, TX, May 2006.
Ginther, O.J. et al. "Effect of a Synthetic Gonadotropin-Releasing Hormone on Plasma Concentrations of Luteinizing Hormone in Ponies," Am. J. Vet. Res., 35: 79-81 (1974).
Ginther, O.J., "Ultrasonic Imaging and Reproductive Events in the Mare," Equiservices, Cross Plains, WI Chapter 4:43-72 (1986).
Ginther, O.J., Reproductive Biology of the Mare: Basic and Applied Aspects, EquiServices, Chapter 12, 499-508 Cross Plains, Wisconsin (1992).
Glajchen, M. "Chronic Pain: Treatment Barriers and Strategies for Clinical Practice." J Am Board Fam Pract. 2001; 14(3): 178-183.
Gomoll, A.H., et al., "Chondrolysis after continuous intra-articular bupivacaine infusion: an experimental model investigating chondrotoxicity in the rabbit shoulder", Arthroscopy: The Journal of Arthroscopic and Related Surgery, vol. 22., No. 8 Aug. 2006. pp. 813-819.
Gorman, G., et al., "Quantitative determination of bupivacaine in plasma from multiple species using LC/MS/MS", slide, ASMS presentation; $53^{rd}$ ASMS Conference, Jun. 5-9, 2005, San Antonio, TX.

(56) References Cited

OTHER PUBLICATIONS

Guevellom, P. Le et al. "High-performance liquid chromatographic determination of bupivacaine in plasma samples for biopharmaceutical studies and application to seven other local anaesthetics," *Journal of Chromatography*, vol. 622, pp. 284-290, 1993.

Gunatillake, P.; Adhikari, R., "Biodegradable synthetic polymers for tissue engineering", *European Cells and Materials*, vol. 5 2003, pp. 1-16.

Hadj, A., et al., "SABER™ Bupivacaine, a novel extended-release formulation of bupivacaine for postoperative pain control demonstrates dose-response, safely and no impact on surgical wound healing following inguinal herniorrhaphy" American College of Surgeons 95th Annual Clinical Congress, Oct. 12, 2009.

Hadj, A., et al., "Safety and efficacy of extended-release bupivacaine local anaesthetic in open hernia repair: a randomized controlled trial", *ANZ Journal of Surgery*, Mar. 11, 2011, pp. 1-7.

Halladay, S., et al., "Pharmacokinetic Evaluation of subcutaneously administered SABER™-bupivacaine (Posidur™) following open inguinal hernia repair", presentation slide, CRS 2006.

Halladay, S., et al., (2006) "Pharmacokinetic evaluation of the SABER™ Delivery system for controlled release of bupivacaine in healthy volunteers", CRS poster.

Harrison, L., et al. "Comparison of HCG, Buserelin and Luprostiol for Induction of Ovulation in Cyclling Mares," J. Eq. Vet. Sci., 11:163-166 (1991).

Hassan, H.G. et al., "Effects of Adjuvants to Local Anaesthetics on their Duration", *Acta Anaesthesial Scand.*, 29, 384-388, 1985.

Hatakeyama et al., "Synthesis and physical properties of polyurethanes from saccharide-based polycaprolactones." Macromolecular Symposia, vol. 130, pp. 127-138, 1998.

Hays LR. "A profile of OxyContin addiction. Journal of Addictive Diseases." 23 (4), 1-9. 2004.

J Heller et al., "Preparation of Polyacetals by the Reaction of Divinyl Ethers and Polyols", *Journal of Polymer Science:* Polymer Letters Edition, vol. 18, 293-297 (1980), pp. 293-297.

J. Heller, "Poly(ortho esters)", *Adv. in Polymer Sci.*, 107, 41-92 (1993).

J. Heller, et al., "Development of a Tetracycline Delivery System for the Treatment of Periodontal Disease Using a Semisolid Poly(Ortho Ester)", APS Research Institute Conference, 5th meeting, 106-110 (1996).

Heller, J., Barr, J., et al., "Poly(ortho esters): Synthesis, characterization, properties and uses", *Adv. Drug Del. Rev.* 54 (2002) 1015-1039.

Heller et al., "Development of poly(ortho esters) and their application for bovine serum albumin and bupivacaine delivery", *J. Contr. Rel.*, vol. 78, No. 1-3, pp. 133-141 (2002).

Heller, J., et al., "Poly(ortho esters)—their development and some recent applications", *Eur J. Pharm Biopharm*, Jul. 2000; 50(1): 121-128.

Heller, J., et al., "Injectable semi-solid poly (ortho esters) for the controlled delivery of therapeutic agents: Synthesis and Applications", *Drug Development & Delivery*, vol. 2, No. 1, Jan./Feb. 2002, Posted Mar. 27, 2008.

Henry, C. (1995) "Sucrose Acetate Isobutyrate Special Grade for Beverage Applications" *International Food Ingred.* pp. 47-49.

Hoskin PJ, et al. "The bioavailability and pharmacokinetics of morphine after intravenous, oral and buccal administration in healthy volunteers." Br J Clin Pharmacol 1989; 27 (4):499-505.

Hyland, J.H. et al. "Infusion of Gonadotrophin-Releasing Hormone (GnRH) Induces of Ovulation and Fertile Oestrus in Mares During Seasonal Anoestrus," J. Reprod. Fert., Suppl. 35 (1987), 211-220.

Inciardi et al. (2007) "Mechanisms of prescription drug diversion among drug-involved club-and street-based populations" Pain Medicine. 8(2), 17 1-183.

Irvine, C.H.G., "GnRH Clinical Application," In Equine Reproduction, (eds) McKinon, A.O. and Voss, J.L., Chapter 36, pp. 41-45, Lea & Febiger (1993).

Irvine, D.S., "Duration of Oestrus and Time of Ovulation in Mares Treated with Synthetic GnRH (Ay24,031)," J. Reprod. Fert. Supp. 23:279-283 (1975).

Ishida T, Oguri K, et al. "Isolation and identitication of urinary metabolites of oxycodone in rabbits." Drug Metab Dispos 1979; 7 (3): 162-5.

Ishida T, Oguri K, Yoshimura H. "Determination of oxycodone metabolites in urines and feces of several mammalian species." J Pharmacobiodyn 1982; 5 (7):52 1-5.

Iyakuhin Tenkabutsu Kenkyykai Ed. "Jitsuyo Iyakuhin Tenkabutsu (Practical Medical Additives)" pub. Kagaku Kogyo-sha Mar. 5, 1974, Tokyo.

Japanese Office Action for Japanese Patent Application No. 2007-532447 dated Nov. 15, 2011.

Jochle, W., et al., Control of Ovulation in the Mare with Ovuplant. TM., a Short-Term Release Implant (STI) Containing the GNRH Analogue Deslorelin Acetate: J. Eq. Vet. Sci., 44:632 (1994).

Johnson & Verity (2002) "Applications of Continuous Site-Directed Drug Delivery" *Proc West Pharmacol Soc* 45:219-222.

Johnston LD, O'Malley PM, Bachman JG, Schulenberg, JE. "Monitoring the future. National results on adolescent drug use: overview of key findings" (NIH Publication No. 05-5726). Bethesda, MD: National Institute on Drug Abuse 2004.

Katz NP, et al. "Behavioral monitoring and urine toxicology testing in patients receiving longterm opioid therapy." Anesth Analg. 97(4), 1097-102.2003.

Katz NP, et al. "Challenges in the development of prescription opioid abuse-deterrent formulations." Clin J Pain. 2007;23(8):648-60.

Katz NP, et al. "Development and preliminary experience with an ease of extractability rating system for prescription opioids." Drug Development and Industrial Pharmacy. 32(6) 727-746(20). 2006.

Katz NP, et al. "Prescription monitoring of medical and non-medical Schedule l/ opioid abuse in Massachusetts: 1996-2005." Conference paper presented at the 69th College on Problems of Drug Dependence (CPDD), Quebec, Canada, 2007.

Kulkarni et al., "Polyactic Acid for Surgical Implants," Arch. Surg., 93:389 (1966).

Lacoste, D., et al., "Reversible Inhibition of Testicular Androgen Secretion by 3-, 5-and 6-Month Controlled-Release Microsphere Formulations of teh LH-RH Agonist [D-Trp.sup.6, des-Gly-NH.sub.2.sup.10 ] LH-RH Ethylamide in the Dog," J. Steroid Biochem. 33:5, 1007-1011 (1989).

Lalovic B, et al. "Pharmacokinetics and pharmacodynamics of oral oxycodone in healthy human subjects: role of circulating active metabolites" Clin Pharmacol Ther 2006; 79 (5):461-79.

Lambert, W.J. et al. "Development of an in situ forming biodegradable poly-lactide-co-glycolide system for controlled release of proteins," *Journal of Controlled Release*, vol. 33, pp. 189-195, 1995.

Loy, R.G. et al. "The Effects of Human Chorionic Gonadotrophin on Ovulation, Length of Estrus, and Fertility in the Mare," Cornell Vet. 56:41-50 (1966).

Mank, R. et al., "Parenterale Depotarzneiformen auf der Basis von biologisch abbaubaren Polymeren", *Die Pharmazie*, 46(1), 9-18, XP-000208772, 1991.

Material Safety Data Sheet of Eastman Chemical Products, "SAIB" Sucrose Acetate Isobutyrate, pp. 2-18. (2004).

Material Safety Data Sheet of Eastman Fine Chemical Pharmaceutical Ingredients, Sucrose Acetate Isobutyrate Special Grade (SAIB-SG), Publication No. EFC-211, (May 1991).

Material Safety Data Sheet of Eastman Products for the Food Industry, "Sucrose Acetate Isobutyrate (SAIB-SB) for Use in Fruit-Flavored Beverages," Publication No. ZM-90, pp. 2-7 (Sep. 1989).

McCabe et al. "Motives, diversion and routes of administration associated with nonmedical use of prescription opioids." Addictive Behaviors. 32, 562-575. 2007.

McCarthy, P. et al., "Management of Stallions on Large Breeding Farms," Stallion Management, vol. 8, No. 1, Apr. 1992, pp. 219-235.

McKinnon, A.O., et al. "Effect of a GnRH Analogue (Ovuplant), hCG and Dexamethasone on Time to Ovulation in Cycling Mares." World Equine Veterinary Review, (1997) 2:3 16-18.

(56) References Cited

OTHER PUBLICATIONS

McKinnon, A.O., et al. "Repeated Use of a GnRH Analogue Deslorelin (Ovuplant) for Hastening Ovulation in the Transitional Mare," Equine Vet. J., (1996) 29:2 153-155.
McLellan AT, Luborsky L, Woody GE, O'Brien CP. "An improved 'diagnostic instrument for substance abuse patients." The Addiction Severity Index. J Nerv Ment Dis. 1980; 168:26-33.
Mearns, "Changing Seasons," The Blood-Horse, Sep. 28, 1996, p. 4794-4795.
Merkli et al (1995) "The use of acidic and basic excipients in the release of 5-fluorouracil and mitomycin C from a semi-solid bioerodible poly (ortho ester)"; Journal of Controlled Release, vol. 33, Issue 3; pp. 415-421.
Merkli et al., "Purity and stability assessment of a semi-solid poly(ortho ester) used in drug delivery systems", Biomaterials, vol. 17, No. 9, pp. 897-902 (1996).
Merrifield, B., "Solid Phase Synthesis" Science 232:342 (1986).
Meyer RJ, et al. Awareness topic: mitigating the risk of ethanol induced dose dumping from oral sustained controlled release dosage forms. In: FDA's Advisory Committee for Pharmaceutical Science Meeting, Oct. 2005.
Moodie, J., et al., "SABER-Bupivacaine Reduces Postoperative Pain Intensity and Opioid Use for 72 Hours in Soft-Tissue and Bony Surgeries", Abstract, American Society of Anesthesiologists, 2014.
Montovan, S.M., et al., "The Effect of a Potent GnRH Agonist on Gonadal and Sexual Activity in the Horse," Theriogenology, 33:6, 1305-1321 (1990).
Moore, P.A., "Long Acting Local Anesthetic: A Review of Clinical Efficacy in Dentistry," Compend. Cont. Ed. Dent., 11, 22-30, 1990.
Mumford, E.L. et al., "Use of Deslorelin Short-Term Implants to Induce Ovulation in Cycling Mares During Three Consecutive Estrov Cycles," Animal Reproduction Science, 139 (1995) 129-140.
Murray S, et al. "Alcohol-associated rapid release of a long-acting opioid" CMAJ 2005; 173(7):756.
Nakagaki "Seizai Butsuri Kagaku (Physical Chemistry of Medical Preparations)", pub. Asakura Shoten, Nov. 5, 1968, Tokyo.
Nally, J., et al., "Induction of Mucosal IgA Specific for SeMF3 for *Streptococcus equi* with Intranasal Vaccination Using a Sucrose Acetate Isobutyrate Based Delivery System", Proceed. Int'l. Symp. Control. Rel. Bioact. Mater., 26 (1999) Controlled Release Society, Inc.
Nett et al., "Further Studies on the Radioimmunoassay of Gonadotropin-Releasing Hormone: Effect of Radioiodination, Antiserum and Unextracted Serum on Levels of Immunoreactivity in Serum," Endocrinology 101:1135 (1977).
Nicholson D., et al., "Post-Operative Pain Control with Extended-Release Bupivacaine Formulation. Clinical Trial Results in Inguinal Hernia Repair." American Hernia Society, Mar. 15, 2008.
Ng, S.Y.; et al., "Synthesis and erosion studies of self-catalyzed poly(ortho ester)s", *Macromolecules*1997, 30 770-772.
Nguyen, et al (1984) "Hydrolysis of some poly(ortho-ester)s in homogeneous solutions"; *J Pharm Sci.* 73(11); pp. 1563-1568.
Okumu, F.W. et al. "Sustained Delivery of Growth Hormone from a Novel Injectable Liquid, Plad," *Proceed. Int'l. Symp. Control. Rel. Bioact. Mater.*, vol. 28, 2001.
Okumu, F.W. et al. "Evaluation of the Saber™ Delivery System for Sustained Release of Growth Hormone—Formulation Design and in Vivo Assessment," *Proceed. Int'l. Symp. Control. Rel. Bioact. Mater.*, vol. 28, 2001.
Papaconstantinou, H., et al., "Intra-incisional depot bupivacaine reduces pain intensity and opioid consumption for 72 hours following openlaparotomy, compared with bupivacaine HC1", Poster, ASCRS conference May 30, 2015-Jun. 3, 2015.
Philip, B.K. et al. "The Economic Impact of Opioids on Postoverative Pain Management," *Journal of Clinical Anesthesia*, vol. 14, pp. 354-364, 2002.
Pulido et al., "Enzymatic Regioselective Acylation of Hexoses and Pentoses Using Oxime Esters.", J. Chem. Soc. Perkin Trans. 1, (21), 2891-2898, 1992.

Rabb et al., "Effects of Active Immunisation Against GnRH on LH, FSH and Prolactin Storage, Sectretion and Response to Their Secretagogues in Pony Geldings," J. Anim Sci., 68:3322-3329.
Reynolds, R.C. et al., "Sucrose acetate isobutyrate (SAIB): historical aspects of its use in beverages and a review of toxicity studies prior to 1988," Food Chem. Toxicol., 1998,36 (2), pp. 8 1-93.
Reynolds, R.C., "Metabolism and pharmacokinetics of sucrose acetate isobutyrate (SAIB) and sucrose octaisobutyrate (SOIB) in rats, dogs, monkeys or humans: a review, " Food Chem Toxicol, 1998,36 (2), pp. 95-99.
Roser, J.J., et al., "The Development of Antibodies to Human Chorionic Gonadotrpins Following its Repeated Injection in the Cyclic Mare," J. Reprod. Fert. Suppl., 173-179 (1979).
Schreier, J., DeLuca, P., "Porous Bone morphogenetic Protein-2 Microspheres: Polymer Binding and in Vitro Release", *AAPS PharmsciTech* 2001; 2(3) art. 17, pp. 1-7.
Schwach-Abdellaoui, K., et al., "Controlled delivery of metoclopramide using an injectable semi-solid poly(ortho ester) for veterinary application", *International Journal of Pharmaceutics*, 2002, 248: 31-37.
Sekar, M., et al., "SABER™ Formulation for Intra-Articular Delivery of rhGH", The American Association of Pharmaceutical Scientists 2009 National Biotechnology Meeting, Jun. 21-25, 2009.
Seymour L. et al., "Poly(ortho ester) matrices for controlled release of the antitumor agent 5-fluorouracil", *J. Controlled Release*, 31, 201-206 (1994).
Shah, J., et al., "Pharmacokinetic Characteristics of SABER-Bupivacaine in Humans Demonstrate Sustained Drug Delivery for up to 72 Hours in a Variety of Surgical Models", American Society of Regional Anesthesia and Pain Medicine (ASRA) Apr. 3-6, 2014.
Shah, J., et al., "The PK Profile of SABER-Bupivacaine in Humans Across Surgical Models Demonstrates Sustained 72-Hour Drug Delivery," Abstract, American Society of Anesthesiologists, 2014.
Shah, J., et al., "Pharmacokinetic characteristics of SABER™-bupivacaine (Posidur™) formulation in humans", APS slide, 2007.
Shih C. et al (1984) "Drug delivery from catalysed erodible polymeric matrices of poly(ortho ester)s"; *Biomaterials.* 5(4); pp. 237-240.
Sintzel, M., et al., Synthesis and characterization of self-catalyzed poly (ortho ester), *Biomaterials* 19, 1998, 791-800.
Sparer R., "Controlled release from erodible poly(ortho ester) drug delivery systems", *J. Contr. Rel.*, 1, 23-32 (1984).
Sullivan, J., "Duration of Estrus and Ovulation Time in Nonlactating Mares Given Human Chorionic Gonadotropin During Three Successive Estrous Periods," J. Am. Vet. Med. Assoc., 63:895 (1973).
Sullivan, S., et al., "Delivery of Taxol and other antineoplastic agents from a novel system based on sucrose acetate isobutyrate", AAPS, Boston, 1997.
Sullivan, S.A., 1998, "Sustained Release of Orally Administered Active Using SABER™ Delivery System Incorporated into Soft Gelatin Capsules" Proceed. Int'l Symp. Control. Rel. Bioact. Mater., 25:918-919.
Swiderski et al., "Application of 14C Isotope in Studies on the Lability of Sugar Substituents" Nukleonika, Supl., vol. 10, pp. 347-352, 1966.
Thompson, Jr., D.L., et al., "Effects of Melatonin and Thyrotropin Releasing Hormone of Mares Durign the Nonbreeding Season," J. Anim Sci., 58:3, 668-677(1983).
Thompson, Jr., D.L., et al., "Testosterone Effects on Mares During Synchronization with Altrenogest: FSH, LH, Estrous, Duration and Pregnancy Rate" J. Anim Sci., 56:3, 678-686 (1983).
Trieger, N. et al., "Bupivacaine and Post-Operative Analgesics in Oral Surgery," Anesthesia Progress, 20-2, 1979.
Trescot AM, et al. "Opioid Guidelines in the Management of Chronic Non-Cancer Pain." Pain Physician. 2006;9: 1-40.
USP XXII, The United States Pharmacopeial Convention, Inc., Bupivacaine, 193-196, 1990.
Vega-Rios A, Villalobos H, Mata-Segreda JF. "Acid-catalyzed hydrolysis of triacylglycerols obeys monoexponential kinetics." Int J Chem Kinet. 1992; 24:887-94.

(56) References Cited

OTHER PUBLICATIONS

Voss, J.L. et al. "The Effect of HCG on Duration of Oestrus, Ovulation Time and Fertility in Mares," J. Reprod. Fert., Suppl. 23 (1975) 297-301.

Watts, R., et al., "Efficacy and Safety of SABER-Bupivacaine Local Anesthetic in Open Hernia Repair," American Society of Regional Anesthesia and Pain Medicine (ASRA) Apr. 3-6, 2014.

Watts, R., et al., "SABER-Bupivacaine Concurrently Reduces Postoperative Pain Intensity and Opioid Use for 72 Hours: Evaluation of CROPIRS Scores," Abstract, American Society of Anesthesiologists, 2014.

Wilson et al. (1999) "Benzyl Alcohol as an Alternative Local Anesthetic" *Ann Emerg Med* 33(5):495-499.

\* cited by examiner

SHORT DURATION DEPOT FORMULATIONS

CROSS REFERENCE TO RELATED APPLICATION

This application is a continuation of U.S. application Ser. No. 15/267,070, filed Sep. 15, 2016, now U.S. Pat. No. 10,201,496, which application is a continuation of U.S. application Ser. No. 11/278,472, filed Apr. 3, 2006, which application is a divisional of U.S. application Ser. No. 10/606,969, filed Jun. 25, 2003, entitled "SHORT DURATION DEPOT FORMULATIONS" which claims the benefit of U.S. Provisional Application No. 60/391,867, filed on Jun. 25, 2002. The contents of the above referenced applications are hereby incorporated in their entirety by reference.

BACKGROUND OF THE INVENTION

Field of the Invention

The present invention relates to a depot gel composition that can be injected into a desired location and which can provide controlled release of a beneficial agent over a short duration of time. The present invention also relates to a method of preparing and administering the composition.

Description of the Related Art

Biodegradable polymers have been used for many years in medical applications. Illustrative devices composed of the biodegradable polymers include sutures, surgical clips, staples, implants, and drug delivery systems. The majority of these biodegradable polymers have been based upon glycolide, lactide, caprolactone, and copolymers thereof.

The biodegradable polymers can be thermoplastic materials, meaning that they can be heated and formed into various shapes such as fibers, clips, staples, pins, films, etc. Alternatively, they can be thermosetting materials formed by crosslinking reactions, which lead to high-molecular-weight materials that do not melt or form flowable liquids at high temperatures. Although thermoplastic and thermosetting biodegradable polymers have many useful biomedical applications, there are several important limitations to their use in the bodies of various animals including humans, animals, birds, fish, and reptiles.

Solid implant drug delivery systems containing a drug incorporated in thermoplastic or thermosetting biodegradable polymers have been widely used successfully. Such implants have to be inserted into the body through an incision which is sometimes larger than desired by the medical profession and occasionally lead to a reluctance of the patients to accept such an implant or drug delivery system. The following U.S. Pat. Nos. 5,456,679; 5,336,057; 5,308,348; 5,279,608; 5,234,693; 5,234,692; 5,209,746; 5,151,093; 5,137,727; 5,112,614; 5,085,866; 5,059,423; 5,057,318; 4,865,845; 4,008,719; 3,987,790 and 3,797,492 are believed to be representative of such drug delivery systems and are incorporated herein by reference. These patents disclose reservoir devices, osmotic delivery devices and pulsatile delivery devices for delivering beneficial agents.

Injecting drug delivery systems as small particles, microspheres, or microcapsules avoids the incision needed to implant drug delivery systems. However, these materials do not always satisfy the demand for a biodegradable implant. These materials are particulate in nature, do not form a continuous film or solid implant with the structural integrity needed for certain prostheses, the particles tend to aggregate and thus their behavior is hard to predict. When inserted into certain body cavities such as a mouth, a periodontal pocket, the eye, or the vagina where there is considerable fluid flow, these small particles, microspheres, or microcapsules are poorly retained because of their small size and discontinuous nature. Further, if there are complications, removal of microcapsule or small-particle systems from the body without extensive surgical intervention is considerably more difficult than with solid implants. Additionally, manufacture, storage and injectability of microspheres or microcapsules prepared from these polymers and containing drugs for release into the body present problems.

The art has developed various drug delivery systems in response to the aforementioned challenges. The following U.S. Pat. Nos. 5,990,194; 5,780,044; 5,733,950; 5,620,700; 5,599,552; 5,556,905 5,278,201; 5,242,910 and 4,938,763; and PCT publication WO 98/27962 are believed to be representative and are incorporated herein by reference. These patents disclose polymer compositions for injectable implants using solvents and/or plasticizers.

Previously described polymer compositions for injectable implants have used solvent/plasticizers that are very or relatively soluble in aqueous body fluids to promote rapid solidification of the polymer at the implant site and promote diffusion of drug from the implant. Rapid migration of water into such polymeric implants utilizing water soluble polymer solvents when the implants are placed in the body and exposed to aqueous body fluids presents a serious problem. The rapid water uptake often results in implants having pore structures that are non-homogeneous in size and shape. Typically, the surface pores take on a finger-like pore structure extending for as much as one-third of a millimeter or more from the implant surface into the implant, and such finger-like pores are open at the surface of the implant to the environment of use. The internal pores tend to be smaller and less accessible to the fluids present in the environment of use. The rapid water uptake characteristic often results in uncontrolled release of beneficial agent that is manifested by an initial, rapid release of beneficial agent from the polymer composition, corresponding to a "burst" of beneficial agent being released from the implant. The burst often results in a substantial portion of the beneficial agent, if not all, being released in a very short time, e.g., hours or 1-2 days. Such an effect can be unacceptable, particularly in those circumstances where a controlled delivery is desired, i.e., delivery of beneficial agent in a controlled manner over a period of greater than or equal to 3 days or up to a month, or where there is a narrow therapeutic window and release of excess beneficial agent can result in adverse consequences to the subject being treated, or where it is necessary to mimic the naturally-occurring daily profile of beneficial agents, such as hormones and the like, in the body of the subject being treated.

Accordingly, when such devices are implanted, the finger-like pores allow very rapid uptake of aqueous body fluids into the interior of the implant with consequent immediate and rapid dissolution of significant quantities of beneficial agent and unimpeded diffusion of beneficial agent into the environment of use, producing the burst effect discussed above.

Furthermore, rapid water uptake can result in premature polymer precipitation such that a hardened implant or one with a hardened skin is produced. The inner pores and much of the interior of the polymer containing beneficial agent are shut off from contact with the body fluids and a significant reduction in the release of beneficial agent can result over a not insignificant period of time ("lag time"). That lag time is undesirable from the standpoint of presenting a controlled, sustained release of beneficial agent to the subject being treated. What one observes, then, is a burst of beneficial agent being released in a short time period immediately after implantation, a lag time in which no or very little beneficial agent is being released, and subsequently continued delivery of beneficial agent (assuming beneficial agent remains after the burst) until the supply of beneficial agent is exhausted.

Various approaches to control burst and modulate and stabilize the delivery of the beneficial agent have been described. The following U.S. Pat. Nos. 6,130,200; 5,990,194; 5,780,044; 5,733,950; 5,656,297; 5,654,010; 4,985,404 and 4,853,218 and PCT publication WO 98/27962 are believed to be representative and are incorporated herein by reference. Notwithstanding some success, those methods have not been entirely satisfactory for the large number of beneficial agents that would be effectively delivered by implants.

SUMMARY OF THE INVENTION

The present invention provides a method and an injectable depot gel composition for systemic and local delivery of a beneficial agent to a subject over a short duration of time. In particular, the invention provides controlled release of the beneficial agent to the subject being treated, the release being controlled over a period equal to or less than two weeks after administration, preferably a period of about 3 to about 7 days. Additionally, the invention provides a method of preparing the injectable depot gel composition.

In one aspect, the invention pertains to an injectable depot composition comprising a low molecular weight bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel. Preferably the solvent has a miscibility in water of less than 7 wt. %, more preferably less than 5 wt %, and more preferably less than 3 wt %.

In another aspect, the invention pertains to an injectable depot composition for systemic delivery of a beneficial agent to a subject in a controlled manner over a duration equal to or less than two weeks comprising a low molecular weight bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel.

In an additional aspect, the invention pertains to an injectable depot composition for sustained delivery of a beneficial agent to a subject comprising a low molecular weight bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel; wherein the beneficial agent is delivered systemically in a controlled manner over a duration equal to or less than two weeks, preferably about 24 hours to about 2 weeks, preferably about 10 days or shorter; preferably about 7 days or shorter, more preferably about 3 days to about 7 days.

In an additional aspect, the invention pertains to an injectable depot composition for sustained delivery of a beneficial agent to a subject comprising a low molecular weight bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel; wherein the beneficial agent is delivered locally in a controlled manner over a duration equal to or less than two weeks, preferably about 24 hours to about 2 weeks, preferably about 10 days or shorter; preferably about 7 days or shorter, more preferably about 3 days to about 7 days.

In another aspect, the invention pertains to an injectable depot composition as described above, further including at least one of the following: a pore former; a solubility modulator for the beneficial agent; and an osmotic agent; and optionally including an emulsifying and/or a thixotropic agent.

In another aspect, the invention pertains to an injectable depot composition as described above, wherein the low molecular weight polymer has a weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000.

In another aspect, the invention pertains to an injectable depot composition as described above, wherein the polymer is selected from the group consisting of polylactides, polyglycolides, polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, chitin, chitosan, hylauronic acid and copolymers, terpolymers and mixtures thereof. In preferred embodiments, the polymer is a lactic acid-based polymer; preferably the polymer is a copolymer of lactic acid and glycolic acid.

In another aspect, the invention pertains to an injectable depot composition as described above, wherein the solvent is selected from an aromatic alcohol having the structural formula (I)

Ar-(L)$_n$-OH    (I)

in which Ar is a substituted or unsubstituted aryl or heteroaryl group, n is zero or 1, and L is a linking moiety; and a solvent selected from the group consisting of esters of aromatic acids, aromatic ketones, and mixtures thereof.

In preferred embodiments, the solvent is selected from the aromatic alcohol, lower alkyl and aralkyl esters of aryl acids; aryl, aralkyl and lower alkyl ketones; and lower alkyl esters of citric acid. Preferably, the solvent is selected from benzyl alcohol, benzyl benzoate and ethyl benzoate. In preferred embodiments, the composition is free of solvents having a miscibility in water that is greater than 7 wt. % at 25° C.

In additional aspects, the invention pertains to methods of administering a beneficial agent to a subject in a controlled manner over a duration equal to or less than two weeks, comprising administering an injectable depot composition as described above. In certain embodiments, the beneficial agent is delivered systemically in a controlled manner over a duration equal to or less than two weeks. In additional embodiments, the beneficial agent is delivered locally in a controlled manner over a duration equal to or less than two weeks. In preferred embodiments, the beneficial agent is delivered over a duration of about 24 hours to about 2 weeks, preferably about 10 days or shorter; preferably about 7 days or shorter, more preferably about 3 days to about 7 days.

In additional aspects, the invention pertains to a kit for administration of a beneficial agent to a subject comprising:

(a) a low molecular weight bioerodible, biocompatible polymer;

(b) a solvent having a miscibility in water of less than or equal to 7 wt. % at 25° C. that is suitable for dissolving the polymer and forming a viscous gel;

(c) a beneficial agent; and optionally, one or more of the following:

(d) an emulsifying agent;

(e) a pore former;

(f) a solubility modulator for the beneficial agent, optionally associated with the beneficial agent; and (g) an osmotic agent;

wherein at least the beneficial agent, optionally associated with the solubility modulator, is maintained separated from the solvent until the time of administration of the beneficial agent to a subject.

In another aspect, the invention pertains to an injectable depot composition and a method of administering such composition as described above, wherein the beneficial agent is selected from a drug, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents, anti-proliferative agents, antimitotic agents, angiogenic agents, antipsychotic agents, central nervous system (CNS) agents, anticoagulants, fibrinolytic agents, growth factors, antibodies, ocular drugs, and metabolites, analogs, derivatives, fragments, and purified, isolated, recombinant and chemically synthesized versions of these species. In preferred embodiments, the beneficial agent is human growth hormone, methionine-human growth hormone; des-phenylalanine human growth hormone, alpha-, beta- or gamma-interferon, erythropoietin, glugacon, calcitonin, heparin, interleukin-1, interleukin-2, Factor VIII, Factor IX, luteinizing hormone, relaxin, follicle-stimulating hormone, atrial natriuretic factor, filgrastim epidermal growth factors (EGFs), platelet-derived growth factor (PDGFs), insulin-like growth factors (IGFs), fibroblast-growth factors (FGFs), transforming-growth factors (TGFs), interleukins (ILs), colony-stimulating factors (CSFs, MCFs, GCSFs, GMCSFs), Interferons (IFNs), endothelial growth factors (VEGF, EGFs), erythropoietin (EPOs), angiopoietins (ANGs), placenta-derived growth factors (PlGFs), and hypoxia induced transcriptional regulators (HIFs). Preferably, the beneficial agent is present in an amount of from 0.1 to 50% by weight of the combined amounts of the polymer, the solvent and the beneficial agent. In preferred embodiments, the beneficial agent is in the form of particles dispersed or dissolved in the viscous gel, wherein the beneficial agent is in the form of particles having an average particle size of from 0.1 to 250 microns. In certain preferred embodiments, the beneficial agent is in the form of particles wherein the particle further comprises a component selected from the group consisting of a stabilizing agent, bulking agent, chelating agent and a buffering agent.

These and other embodiments of the present invention will readily occur to those of ordinary skill in the art in view of the disclosure herein.

BRIEF DESCRIPTION OF THE DRAWINGS

The foregoing and other objects, features and advantages of the present invention will be more readily understood upon reading the following detailed description in conjunction with the drawings as described hereinafter.

DETAILED DESCRIPTION OF THE INVENTION

Figure 1:
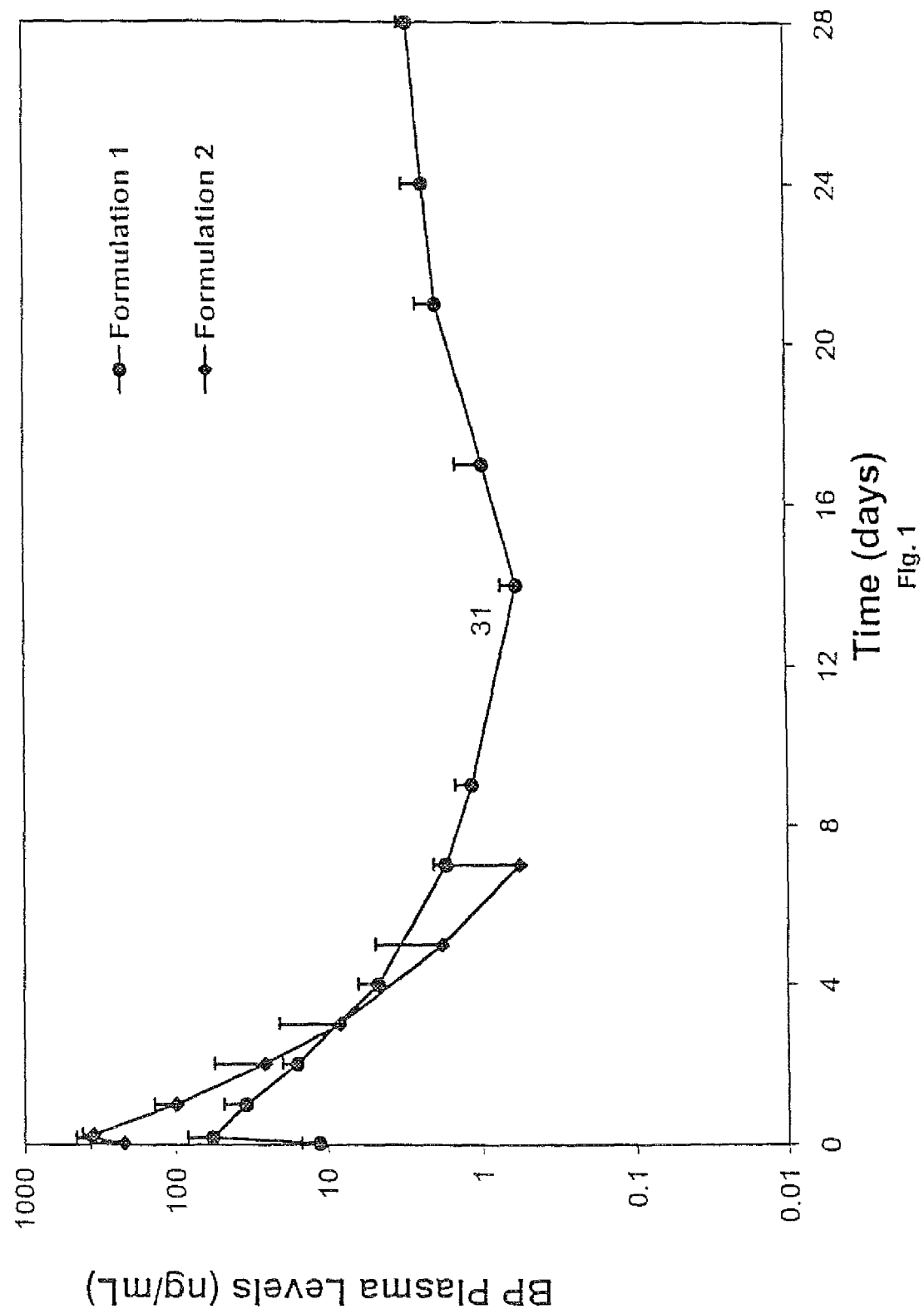
FIG. 1 is a graph illustrating the in vivo release profile of bupivacaine hydrochloride obtained from depot formulations of the present invention (formulations 1-2).

The present invention is directed to an injectable depot composition that serves as an implanted sustained release beneficial agent delivery system after injection into a patient's body. The composition is a gel formed from a low molecular weight bioerodible, biocompatible polymer; a solvent having a miscibility in water of less than or equal to 7 wt. % at 25° C., in an amount effective to plasticize the polymer and form a gel therewith; and a beneficial agent dissolved or dispersed in the gel. The present invention is also directed to a method of systemically or locally administering a beneficial agent to a subject by implanting in the subject an injectable depot composition as described above. By appropriate choice of solvent, water migration from the aqueous environment surrounding the implant system is restricted, and beneficial agent is released to the subject over a period of time, thus providing for delivery of the beneficial agent with a controlled burst of beneficial agent and sustained release thereafter. The duration and the rate of release of the beneficial agent are controlled by appropriate choice of the low molecular weight biodegradable polymer. The composition provides controlled sustained release of the beneficial agent by restricting water migration from the aqueous environment surrounding the implant system, thus delivering the beneficial agent over a short duration, preferably a period equal to or less than two weeks, preferably about 24 hours to about 2 weeks, preferably about 10 days or shorter; preferably about 7 days or shorter, more preferably about 3 days to about 7 days. Because the polymer of the composition is bioerodible, the implant system does not have to be surgically removed after beneficial agent is depleted from the implant.

Generally, the compositions of the invention are gel-like and faun with a substantially homogeneous non-porous structure throughout the implant upon implantation and during drug delivery, even as it hardens. Furthermore, while the polymer gel implant will slowly harden when subjected to an aqueous environment, the hardened implant may maintain a rubbery (non-rigid) composition with the glass transition temperature $T_g$ being below 37° C.

It has been discovered that when a solvent having a solubility in water of less than 7% by weight in water is present in the system, suitable burst control and sustained delivery of beneficial agent is achieved, whether or not a solubility modulator of the beneficial agent is present in the system. Typically, the implant systems useful in this invention will release, in the first 24 hours after implantation, 40% or less of the total amount of beneficial agent to be delivered to the subject from the implant system, preferably 30% or less and more preferably 20% or less. In certain embodiments, within 24 hours after implantation the system releases less than or equal to 20% by weight of the amount of beneficial agent to be delivered over the duration of the delivery period, wherein the delivery period is 2 weeks. In additional embodiments, within 24 hours after implantation the system releases less than or equal to 40% by weight of the amount of beneficial agent to be delivered over the duration of the delivery period, wherein the delivery period is one week. In additional embodiments, within 24 hours after implantation the system releases less than or equal to 50% by weight of the amount of beneficial agent to be delivered over the duration of the delivery period, wherein the delivery period is three days.

When the composition is intended for implantation by injection, the viscosity optionally may be modified by emulsifiers and/or thixotropic agents to obtain a gel composition having a viscosity low enough to permit passage of the gel composition through a needle. Also, pore formers and solubility modulators of the beneficial agent may be added to the implant systems to provide desired release profiles from the implant systems, along with typical pharmaceutical excipients and other additives that do not change the beneficial aspects of the present invention. The addition of a solubility modulator to the implant system may enable the use of a solvent having a solubility of 7% or greater in the implant system with minimal burst and sustained delivery under particular circumstances. However, it is presently preferred that the implant system utilize at least one solvent having a solubility in water of less than 7% by weight, whether the solvent is present alone or as part of a solvent mixture. It has also been discovered that when mixtures of solvents which include a solvent having 7% or less by weight solubility in water and one or more miscible solvents, optionally having greater solubility, are used, implant systems exhibiting limited water uptake and minimal burst and sustained delivery characteristics are obtained.

Definitions

In describing and claiming the present invention, the following terminology will be used in accordance with the definitions set out below.

The singular forms "a," "an" and "the" include plural referents unless the context clearly dictates otherwise. Thus, for example, reference to "a solvent" includes a single solvent as well as a mixture of two or more different solvents, reference to "a beneficial agent" includes a single beneficial agent as well as two or more different beneficial agents in combination, and the like.

The term "beneficial agent" means an agent that effects a desired beneficial, often pharmacological, effect upon administration to a human or an animal, whether alone or in combination with other pharmaceutical excipients or inert ingredients.

As used herein, the term "polynucleotide" refers to a polymeric form of nucleotides of any length, either ribonucleotides or deoxyribonucleotides, and includes double- and single-stranded DNA and RNA. It also includes known types of modifications, substitutions, and internucleotide modifications, which are known in the art.

As used herein, the term "recombinant polynucleotide" refers to a polynucleotide of genomic, cDNA, semisynthetic, or synthetic origin which, by virtue of its origin or manipulation: is not associated with all or a portion of a polynucleotide with which it is associated in nature; is linked to a polynucleotide other than that to which it is linked in nature; or does not occur in nature.

As used herein, the term "polypeptide" refers to a polymer of amino acids, including for example, peptides, oligopeptides, and proteins and derivatives, analogs and fragments thereof, as well as other modifications known in the art, both naturally occurring and non-naturally occurring.

As used herein, the term "purified" and "isolated" when referring to a polypeptide or nucleotide sequence means that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type present.

The term "AUC" means the area under the curve obtained from an in vivo assay in a subject by plotting blood plasma concentration of the beneficial agent in the subject against time, as measured from the time of implantation of the composition, to a time "t" after implantation. The time t will correspond to the delivery period of beneficial agent to a subject.

The term "burst index" means, with respect to a particular composition intended for systemic delivery of a beneficial agent, the quotient formed by dividing (i) the AUC calculated for the first time period after implantation of the composition into a subject divided by the number of hours in the first time period ($t_1$), by (ii) the AUC calculated for the time period of delivery of beneficial agent, divided by the number of hours in the total duration of the delivery period ($t_2$). For example the burst index at 24 hours is the quotient formed by dividing (i) the AUC calculated for the first twenty-four hours after implantation of the composition into a subject divided by the number 24, by (ii) the AUC calculated for the time period of delivery of beneficial agent, divided by the number of hours in the total duration of the delivery period.

The phrase "dissolved or dispersed" is intended to encompass all means of establishing a presence of beneficial agent in the gel composition and includes dissolution, dispersion, suspension and the like.

The term "systemic" means, with respect to delivery or administration of a beneficial agent to a subject, that the beneficial agent is detectable at a biologically-significant level in the blood plasma of the subject.

The term "local" means, with respect to delivery or administration of a beneficial agent to a subject, that the beneficial agent is delivered to a localized site in the subject but is not detectable at a biologically significant level in the blood plasma of the subject.

The terms "short period" or "short duration" are used interchangeably and refer to a period of time over which release of a beneficial agent from the depot gel composition of the invention occurs, which will generally be equal to or less than two weeks, preferably about 24 hours to about 2 weeks, preferably about 10 days or shorter; preferably about 7 days or shorter, more preferably about 3 days to about 7 days.

The term "gel vehicle" means the composition formed by mixture of the polymer and solvent in the absence of the beneficial agent.

The term "initial burst" means, with respect to a particular composition of this invention, the quotient obtained by dividing (i) the amount by weight of beneficial agent released from the composition in a predetermined initial period of time after implantation, by (ii) the total amount of beneficial agent that is to be delivered from an implanted composition. It is understood that the initial burst may vary depending on the shape and surface area of the implant. Accordingly, the percentages and burst indices associated with initial burst described herein are intended to apply to compositions tested in a form resulting from dispensing of the composition from a standard syringe.

The term "solubility modulator" means, with respect to the beneficial agent, an agent that will alter the solubility of the beneficial agent, with reference to polymer solvent or water, from the solubility of beneficial agent in the absence of the modulator. The modulator may enhance or retard the solubility of the beneficial agent in the solvent or water. However, in the case of beneficial agents that are highly water soluble, the solubility modulator will generally be an agent that will retard the solubility of the beneficial agent in water. The effects of solubility modulators of the beneficial agent may result from interaction of the solubility modulator with the solvent, or with the beneficial agent itself, such as by the formation of complexes, or with both. For the purposes hereof, when the solubility modulator is "associated" with the beneficial agent, all such interactions or formations as may occur are intended. Solubility modulators may be mixed with the beneficial agent prior to its combination with the viscous gel or may be added to the viscous gel prior to the addition of the beneficial agent, as appropriate.

The terms "subject" and "patient" mean, with respect to the administration of a composition of the invention, an animal or a human being.

Since all solvents, at least on a molecular level, will be soluble in water (i.e., miscible with water) to some very limited extent, the term "immiscible" as used herein means that 7% or less by weight, preferably 5% or less, of the solvent is soluble in or miscible with water. For the purposes of this disclosure, solubility values of solvent in water are considered to be determined at 25° C. Since it is generally recognized that solubility values as reported may not always be conducted at the same conditions, solubility limits recited herein as percent by weight miscible or soluble with water as part of a range or upper limit may not be absolute. For example, if the upper limit on solvent solubility in water is recited herein as "7% by weight," and no further limitations on the solvent are provided, the solvent "triacetin," which has a reported solubility in water of 7.17 grams in 100 ml of water, is considered to be included within the limit of 7%. A solubility limit in water of less than 7% by weight as used herein does not include the solvent triacetin or solvents having solubilities in water equal to or greater than triacetin.

The term "bioerodible" refers to a material that gradually decomposes, dissolves, hydrolyzes and/or erodes in situ. Generally, the "bioerodible" polymers herein are polymers that are hydrolyzable, and bioerode in situ primarily through hydrolysis.

The term "thixotropic" is used in its conventional sense to refer to a gel composition that can liquefy or at least exhibit a decrease in apparent viscosity upon application of mechanical force such as shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe which temporarily reduces its viscosity during the injection process. When the injection process is completed, the shearing force is removed and the gel returns very near to its previous state.

A "thixotropic agent" as used herein is one that increases the thixotropy of the composition in which it is contained, promoting shear thinning and enabling use of reduced injection force.

The term "low molecular weight (LMW) polymer" refers to bioerodible polymers having a weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000 as determined by gel permeation chromatography (GPC).

The term "high molecular weight (HMW) polymer" refers to bioerodible polymers having a weight average molecular weight greater than 10,000 as determined by gel permeation chromatography (GPC).

The polymer, solvent and other agents of the invention must be "biocompatible"; that is they must not cause irritation, inflammation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal.

The following definitions apply to the molecular structures described herein:

As used herein, the phrase "having the formula" or "having the structure" is not intended to be limiting and is used in the same way that the term "comprising" is commonly used.

The term "alkyl" as used herein refers to a saturated hydrocarbon group typically although not necessarily containing 1 to about 30 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl or lower alkyl.

The term "aryl" as used herein, and unless otherwise specified, refers to an aromatic substituent containing a single aromatic ring or multiple aromatic rings that are fused together, linked covalently, or linked to a common group such as a methylene or ethylene moiety. Preferred aryl groups contain one aromatic ring or two fused or linked aromatic rings, e.g., phenyl, naphthyl, biphenyl, diphenylether, diphenylamine, benzophenone, and the like, and most preferred aryl groups are monocyclic. "Substituted aryl" refers to an aryl moiety substituted with one or more substituent groups, and the terms "heteroatom-containing aryl" and "heteroaryl" refer to aryl in which at least one carbon atom is replaced with a heteroatom. Unless otherwise indicated, the term "aryl" includes heteroaryl, substituted aryl, and substituted heteroaryl groups.

The term "aralkyl" refers to an alkyl group substituted with an aryl group, wherein alkyl and aryl are as defined above. The term "heteroaralkyl" refers to an alkyl group substituted with a heteroaryl group. Unless otherwise indicated, the term "aralkyl" includes heteroaralkyl and substituted aralkyl groups as well as unsubstituted aralkyl groups. Generally, the term "aralkyl" herein refers to an arylsubstituted lower alkyl group, preferably a phenyl substituted lower alkyl group such as benzyl, phenethyl, 1-phenylpropyl, 2-phenylpropyl, and the like.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heterocyclic" refers to a cyclic substituent that is heteroatom-containing, the term "heteroaryl" refers to an aryl substituent that is heteroatom-containing, and the like.

By "substituted" as in "substituted alkyl," "substituted aryl" and the like, as alluded to in some of the aforementioned definitions, is meant that in the alkyl or aryl moiety, respectively, at least one hydrogen atom bound to a carbon atom is replaced with one or more non-interfering substituents such as hydroxyl, alkoxy, thio, amino, halo, and the like.

I. Injectable Depot Compositions:

As described previously, injectable depot compositions for delivery of beneficial agents over a short duration of time may be formed as viscous gels prior to injection of the depot into a subject. The viscous gel supports dispersed beneficial agent to provide appropriate delivery profiles, which include those having low initial burst, of the beneficial agent as the beneficial agent is released from the depot over time.

The polymer, solvent and other agents of the invention must be biocompatible; that is they must not cause irritation or necrosis in the environment of use. The environment of use is a fluid environment and may comprise a subcutaneous, intramuscular, intravascular (high/low flow), intramyocardial, adventitial, intratumoral, or intracerebral portion, wound sites, tight joint spaces or body cavity of a human or animal. In certain embodiments, the beneficial agent may be administered locally to avoid or minimize systemic side effects. Gels of the present invention containing a beneficial agent may be injected/implanted directly into or applied as a coating to the desired location, e.g., subcutaneous, intramuscular, intravascular, intramyocardial, adventitial, intratumoral, or intracerebral portion, wound sites, tight joint spaces or body cavity of a human or animal.

Typically, the viscous gel will be injected from a standard hypodermic syringe, a catheter or a trocar, that has been pre-filled with the beneficial agent-viscous gel composition as the depot. It is often preferred that injections take place using the smallest size needle (i.e., smallest diameter) or catheter to reduce discomfort to the subject when the injection is in a subcutaneous, intramuscular, intravascular (high/low flow), intramyocardial, adventitial, intratumoral, or intracerebral portion, wound sites, tight joint spaces or body cavity of a human or animal. It is desirable to be able to inject gels through a needle or a catheter ranging from 16 gauge and higher, preferably 20 gauge and higher, more preferably 22 gauge and higher, even more preferably 24 gauge and higher. With highly viscous gels, i.e., gels having a viscosity of about 100 poise or greater, injection forces to dispense the gel from a syringe having a needle in the 20-30 gauge range may be so high as to make the injection difficult or reasonably impossible when done manually. At the same time, the high viscosity of the gel is desirable to maintain the integrity of the depot after injection and during the dispensing period and also facilitate desired suspension characteristics of the beneficial agent in the gel.

A composition of a polymer and polymer solvent that optionally includes an agent that imparts thixotropic characteristics to the viscous gel formed by the polymer solvent and polymer provides certain advantages. A thixotropic gel exhibits reduced viscosity when subjected to shear force. The extent of the reduction is in part a function of the shear rate of the gel when subjected to the shearing force. When the shearing force is removed, the viscosity of the thixotropic gel returns to a viscosity at or near that which it displayed prior to being subjected to the shearing force. Accordingly, a thixotropic gel may be subjected to a shearing force when injected from a syringe or a catheter, which temporarily reduces its viscosity during the injection process. When the injection process is completed, the shearing force is removed and the gel returns very near to its previous state.

Significant shear thinning properties of the injectable composition allow for a minimally invasive delivery, via a needle or a catheter, of a beneficial agent to various sites on an external and/or internal surface of the body. Further injection through the needle or injection catheter permits precise administration of a desirable amount of the composition at a desired location, with significant retention of the depot gel composition at the site of delivery while providing for sustained delivery of the beneficial agent from the site of administration. In certain embodiments, the injection catheter may include a metering device or an additional device to assist in the precise delivery of the composition.

A. The Bioerodible, Biocompatible Polymer:

Polymers that are useful in conjunction with the methods and compositions of the invention are bioerodible, i.e., they gradually degrade e.g., enzymatically or hydrolyze, dissolve, physically erode, or otherwise disintegrate within the aqueous fluids of a patient's body. Generally, the polymers bioerode as a result of hydrolysis or physical erosion, although the primary bioerosion process is typically hydrolysis or enzymatic degradation.

Such polymers include, but are not limited to polylactides, polyglycolides, polyanhydrides, polyamines, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polyphosphoesters, chitin, chitosan, hylauronic acid and copolymers, terpolymers and mixtures thereof.

The low molecular weight bioerodible polymers have weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000 as determined by gel permeation chromatography (GPC).

Presently preferred polymers are polylactides, that is, a lactic acid-based polymer that can be based solely on lactic acid or can be a copolymer based on lactic acid and glycolic acid which may include small amounts of other comonomers that do not substantially affect the advantageous results which can be achieved in accordance with the present invention. As used herein, the term "lactic acid" includes the isomers L-lactic acid, D-lactic acid, DL-lactic acid and lactide while the term "glycolic acid" includes glycolide. Most preferred are poly(lactide-co-glycolide)copolymers, commonly referred to as PLGA. The polymer may have a monomer ratio of lactic acid/glycolic acid of from about 100:0 to about 15:85, preferably from about 60:40 to about 75:25 and an especially useful copolymer has a monomer ratio of lactic acid/glycolic acid of about 50:50.

The lactic acid-based polymer has a weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000 as determined by gel permeation chromatography (GPC). As indicated in aforementioned U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000, and a wide variety of end groups to alter susceptibility to hydrolysis and subsequent breakdown of the polymer chain are available from Boehringer Ingelheim (Petersburg, Va.).

Examples of polymers include, but are not limited to, Poly (D,L-lactide-co-glycolide) 50:50 Resomer® RG502, code 0000366, Poly (D,L-lactide-co-glycolide) 50:50 Resomer® RG502H, PLGA-502H, code no. 260187, Poly D,L Lactide (Resomer® R 202, Resomer® R 203); Poly dioxanone (Resomer® X 210) (Boehringer Ingelheim Chemicals, Inc., Petersburg, Va.).

Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lacticle-co-caprolactone 25:75; and Poly DL-lactide-co-caprolactone 75:25 (Birmingham Polymers, Inc., Birmingham, Ala.).

It has been surprisingly found that injectable depot gel formulations of the invention comprising low molecular weight polymers provide a controlled, sustained release of a beneficial agent over a short duration of time equal to or less than two weeks. The release rate profile can be controlled by the appropriate choice of a low molecular weight polymer, a water immiscible solvent, the polymer/solvent ratio, emulsifying agent, thixotropic agent, pore former, solubility modifier for the beneficial agent, an osmotic agent, and the like The biocompatible polymer is present in the gel composition in an amount ranging from about 5 to about 90% by weight, preferably from about 10 to about 85% by weight, preferably from about 15 to about 80% by weight, preferably from about 20 to about 75% by weight, preferably from about 30 to about 70% by weight and typically from about 35 to about 65%, and often about 40 to about 60% by weight of the viscous gel, the viscous gel comprising the combined amounts of the biocompatible polymer and the solvent. The solvent will be added to polymer in amounts described below, to provide injectable depot gel compositions.

B. Solvents and Agents:

The injectable depot composition of the invention contains a water-immiscible solvent in addition to the bioerodible polymer and the beneficial agent. In preferred embodiments, the compositions described herein are also free of solvents having a miscibility in water that is greater than 7 wt. % at 25° C.

The solvent must be biocompatible, should form a viscous gel with the polymer, and restrict water uptake into the implant. The solvent may be a single solvent or a mixture of solvents exhibiting the foregoing properties. The term "solvent", unless specifically indicated otherwise, means a single solvent or a mixture of solvents. Suitable solvents will substantially restrict the uptake of water by the implant and may be characterized as immiscible in water, i.e., having a solubility in water of less than 7% by weight. Preferably, the solvents are five weight percent or less soluble in water; more preferably three weight percent or less soluble in water; and even more preferably one weight percent or less soluble in water. Most preferably the solubility of the solvent in water is equal to or less than 0.5 weight percent.

Water miscibility may be determined experimentally as follows: Water (1-5 g) is placed in a tared clear container at a controlled temperature, about 20° C., and weighed, and a candidate solvent is added dropwise. The solution is swirled to observe phase separation. When the saturation point appears to be reached, as determined by observation of phase separation, the solution is allowed to stand overnight and is re-checked the following day. If the solution is still saturated, as determined by observation of phase separation, then the percent (w/w) of solvent added is determined. Otherwise more solvent is added and the process repeated.

Solubility or miscibility is determined by dividing the total weight of solvent added by the final weight of the solvent/water mixture. When solvent mixtures are used, for example 20% triacetin and 80% benzyl benzoate, they are pre-mixed prior to adding to the water.

Solvents useful in this invention are generally less than 7% water soluble by weight as described above. Solvents having the above solubility parameter may be selected from aromatic alcohols, the lower alkyl and aralkyl esters of aryl acids such as benzoic acid, the phthalic acids, salicylic acid, lower alkyl esters of citric acid, such as triethyl citrate and tributyl citrate and the like, and aryl, aralkyl and lower alkyl ketones. Among preferred solvents are those having solubilities within the foregoing range selected from compounds having the following structural formulas (I), (II) and (III). The aromatic alcohol has the structural formula (I)

Ar-(L)$_n$-OH   (I)

wherein Ar is a substituted or unsubstituted aryl or heteroaryl group, n is zero or 1, and L is a linking moiety. Preferably, Ar is a monocyclic aryl or heteroaryl group, optionally substituted with one or more noninterfering substituents such as hydroxyl, alkoxy, thio, amino, halo, and the like. More preferably, Ar is an unsubstituted 5- or 6-membered aryl or heteroaryl group such as phenyl, cyclopentadienyl, pyridinyl, pyrimadinyl, pyrazinyl, pyrrolyl, pyrazolyl, imidazolyl, furanyl, thiophenyl, thiazolyl, isothiazolyl, or the like. The subscript "n" is zero or 1, meaning that the linking moiety L may or may not be present. Preferably, n is 1 and L is generally a lower alkylene linkage such as methylene or ethylene, wherein the linkage may include heteroatoms such as O, N or S. Most preferably, Ar is phenyl, n is 1, and L is methylene, such that the aromatic alcohol is benzyl alcohol.

The aromatic acid ester or ketone may be selected from the lower alkyl and aralkyl esters of aromatic acids, and aryl and aralkyl ketones. Generally, although not necessarily, the aromatic acid esters and ketones will respectively have the structural formula (II) or (III)

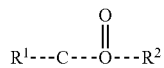

$$R^1-C(=O)-O-R^2 \quad (II)$$

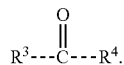

$$R^3-C(=O)-R^4. \quad (III)$$

In the ester of formula (II), $R^1$ is substituted or unsubstituted aryl, aralkyl, heteroaryl or heteroaralkyl, preferably substituted or unsubstituted aryl or heteroaryl, more preferably monocyclic or bicyclic aryl or heteroaryl optionally substituted with one or more non-interfering substituents such as hydroxyl, carboxyl, alkoxy, thio, amino, halo, and the like, still more preferably 5- or 6-membered aryl or heteroaryl such as phenyl, cyclopentadienyl, pyridinyl, pyrimadinyl, pyrazinyl, pyrrolyl, pyrazolyl, imidazolyl, furanyl, thiophenyl, thiazolyl, or isothiazolyl, and most preferably 5- or 6-membered aryl. $R^2$ is hydrocarbyl or heteroatom-substituted hydrocarbyl, typically lower alkyl or substituted or unsubstituted aryl, aralkyl, heteroaryl or heteroaralkyl, preferably lower alkyl or substituted or unsubstituted aralkyl or heteroaralkyl, more preferably lower alkyl or monocyclic or bicyclic aralkyl or heteroaralkyl optionally substituted with one or more non-interfering substituents such as hydroxyl, carboxyl, alkoxy, thio, amino, halo, and the like, still more preferably lower alkyl or 5- or 6-membered aralkyl or heteroaralkyl, and most preferably lower alkyl or 5- or 6-membered aryl optionally substituted with one or more additional ester groups having the structure —O—(CO)—$R^1$. Most preferred esters are benzoic acid and phthalic acid derivatives.

In the ketone of formula (III), $R^3$ and $R^4$ may be selected from any of the $R^1$ and $R^2$ groups identified above.

Art recognized benzoic acid derivatives from which solvents having the requisite solubility may be selected include, without limitation: 1,4-cyclohexane dimethanol dibenzoate, diethylene glycol dibenzoate, dipropylene glycol dibenzoate, polypropylene glycol dibenzoate, propylene glycol dibenzoate, diethylene glycol benzoate and dipropylene glycol benzoate blend, polyethylene glycol (200) dibenzoate, isodecyl benzoate, neopentyl glycol dibenzoate, glyceryl tribenzoate, pentaerylthritol tetrabenzoate, cumylphenyl benzoate, trimethyl pentanediol dibenzoate.

Art recognized phthalic acid derivatives from which solvents having the requisite solubility may be selected include: Alkyl benzyl phthalate, bis-cumyl-phenyl isophthalate, dibutoxyethyl phthalate, dimethyl phthalate, dimethyl phthalate, diethyl phthalate, dibutyl phthalate, diisobutyl phthalate, butyl octyl phthalate, diisoheptyl phthalate, butyl octyl phthalate, diisononyl phthalate, nonyl undecyl phthalate, dioctyl phthalate, di-isooctyl phthalate, dicapryl phthalate, mixed alcohol phthalate, di-(2-ethylhexyl) phthalate, linear heptyl, nonyl, phthalate, linear heptyl, nonyl, undecyl phthalate, linear nonyl phthalate, linear nonyl undecyl phthalate, linear dinonyl, didecyl phthalate (diisodecyl phthalate), diundecyl phthalate, ditridecyl phthalate, undecyldodecyl phthalate, decyltridecyl phthalate, blend (50/50) of dioctyl and didecyl phthalates, butyl benzyl phthalate, and dicyclohexyl phthalate.

Many of the solvents useful in the invention are available commercially (Aldrich Chemicals, Sigma Chemicals) or may be prepared by conventional esterification of the respective arylalkanoic acids using acid halides, and optionally esterification catalysts, such as described in U.S. Pat. No. 5,556,905, which is incorporated herein by reference, and in the case of ketones, oxidation of their respective secondary alcohol precursors.

Preferred solvents include aromatic alcohols, the lower alkyl and aralkyl esters of the aryl acids described above. Representative acids are benzoic acid and the phthalic acids, such as phthalic acid, isophthalic acid, and terephathalic acid. Most preferred solvents are benzyl alcohol and derivatives of benzoic acid and include, but are not limited to, methyl benzoate, ethyl benzoate, n-propyl benzoate, isopropyl benzoate, butyl benzoate, isobutyl benzoate, sec-butyl benzoate, tert-butyl benzoate, isoamyl benzoate and benzyl benzoate, with benzyl benzoate being most especially preferred.

The composition may also include, in addition to the water-immiscible solvent(s), one or more additional miscible solvents ("component solvents"), provided that any such additional solvent is other than a lower alkanol. Component solvents compatible and miscible with the primary solvent(s) may have a higher miscibility with water and the resulting mixtures may still exhibit significant restriction of water uptake into the implant. Such mixtures will be referred to as "component solvent mixtures." Useful component solvent mixtures may exhibit solubilities in water greater than the primary solvents themselves, typically between 0.1 weight percent and up to and including 50 weight percent, preferably up to and including 30 weight percent, and most preferably up to an including 10 weight percent, without detrimentally affecting the restriction of water uptake exhibited by the implants of the invention.

Component solvents useful in component solvent mixtures are those solvents that are miscible with the primary solvent or solvent mixture, and include, but are not limited, to triacetin, diacetin, tributyrin, triethyl citrate, tributyl citrate, acetyl triethyl citrate, acetyl tributyl citrate, triethylglycerides, triethyl phosphate, diethyl phthalate, diethyl tartrate, mineral oil, polybutene, silicone fluid, glylcerin, ethylene glycol, polyethylene glycol, octanol, ethyl lactate, propylene glycol, propylene carbonate, ethylene carbonate, butyrolactone, ethylene oxide, propylene oxide, N-methyl-2-pyrrolidone, 2-pyrrolidone, glycerol formal, methyl acetate, ethyl acetate, methyl ethyl ketone, dimethylformamide, dimethyl sulfoxide, tetrahydrofuran, caprolactam, decyhnethylsulfoxide, oleic acid, and 1-dodecylazacycloheptan-2-one, and mixtures thereof.

Preferred solvent mixtures are those in which benzyl benzoate is the primary solvent, and mixtures formed of benzyl benzoate and either triacetin, tributyl citrate, triethyl citrate or N-methyl-2-pyrrolidone. Preferred mixtures are those in which benzyl benzoate is present by weight in an amount of 50% or more, more preferably 60% or more and most preferably 80% or more of the total amount of solvent present. Especially preferred mixtures are those of 80/20 mixtures by weight of benzyl benzoate/triacetin and benzyl benzoate/N-methyl-2-pyrrolidone. In additional embodiments, the preferred solvent is benzyl alcohol, and mixtures formed of benzyl alcohol and either benzyl benzoate or ethyl benzoate. Preferred mixtures of benzyl alcohol/benzyl benzoate and benzyl alcohol/ethyl benzoate are 1/99 mixtures by weight; 20/80 mixtures by weight; 30/70 mixtures by weight; 50/50 mixtures by weight; 70/30 mixtures by weight; 80/20 mixtures by weight; 99/1 mixtures by weight. Especially preferred mixtures of benzyl alcohol/benzyl benzoate and benzyl alcohol/ethyl benzoate are 25/75 mixtures by weight and 75/25 mixtures by weight.

In an especially preferred embodiment, the primary solvent is selected from an aromatic alcohol and lower alkyl and aralkyl esters of benzoic acid and the polymer is a lactic-acid based polymer, most preferably PLGA, having weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000. Presently, the most preferred solvents are benzyl alcohol, benzyl benzoate and the lower alkyl esters of benzoic acid, e.g. ethyl benzoate. The primary solvents, e.g., aromatic alcohol and benzoic acid esters may be used alone or in a mixture with other miscible solvents, e.g., triacetin, as described herein.

The solvent or solvent mixture is capable of dissolving the polymer to form a viscous gel that can maintain particles of the beneficial agent dissolved or dispersed and isolated from the environment of use prior to release. The compositions of the present invention provide implants useful both for systemic and local administration of beneficial agent, the implants having a low burst index. Water uptake is controlled by the use of a solvent or component solvent mixture that solublizes or plasticizes the polymer but substantially restricts uptake of water into implant. Additionally, the preferred compositions may provide viscous gels that have a glass transition temperature that is less than 37° C., such that the gel remains non-rigid for a period of time after implantation of 24 hours or more.

The importance of restriction of water uptake and the appropriate choice of a low molecular weight polymer and a water immiscible solvent for a controlled, sustained delivery over a short duration can be appreciated by reference to FIGS. 1-10 illustrating in vivo release rate profiles for various compositions as a function of time.

The solvent or solvent mixture is typically present in an amount of from about 95 to about 10% by weight, preferably from about 80 to about 20% by weight, preferably about 75 to about 15% by weight, preferably from about 70 to about 20% by weight, preferably about 65 to about 20% by weight, preferably about 65 to about 30% by weight and often about 60 to about 40% by weight of the viscous gel, i.e., the combined amounts of the polymer and the solvent. The polymer to solvent ratio ranges from about 30:70 to about 90:10 by weight; preferably about 40:60 to about 80:20 by weight; preferably about 50:50 to about 75:25 by weight; and more preferably about 55:45 to about 65:35 by weight.

In addition to the control of water uptake and associated initial burst by choice of solvent, agents that modulate the water solubility of the beneficial agent can also be utilized in conjunction with the preferred solvents to control burst of beneficial agent from the implant. Burst indices and percent of beneficial agent released in the first twenty-four hours after implantation may be reduced by one-third to two-thirds or more by the use of solubility modulators associated with the beneficial agent. Such modulators are typically coatings, substances that form complexes or otherwise associate with or stabilize the beneficial agent such as metallic ions, other stabilizing agents, waxes, lipids, oils, non-polar emulsions, and the like. Use of such solubility modulators may permit the use of more highly water soluble solvents or mixtures and achieve burst indices of 8 or less for systemic applications, or with respect to local applications, release of beneficial agent in the first 24 hours after implantation of not greater than 40% of the beneficial agent administered. Preferably that release will be not greater than 30% and more preferably not greater than 20%.

Limited water uptake by the compositions of this invention can often provide the opportunity to prepare compositions without solubility modulators when in other compositions such modulators would be necessary.

In instances where the choice of solvent and polymer result in compositions severely restricting water uptake by themselves, it may be desirable to add osmotic agents or other agents and hydroattractants that facilitate water uptake to desired levels. Such agents may be, for example, sugars and the like, and are well known in the art.

Limited water uptake by the solvent-polymer compositions of the present invention results in the implant compositions being formed without the finger-like pores in the surface of implants formed using prior art processes. Typically, a composition of the present invention takes the form of a substantially, homogeneous, sponge-like gel, with the pores in the interior of the implant being much the same as the pores on the surface of the implant. Compositions of the present invention retain their gel-like consistency and administer a beneficial agent in a controlled manner, at a sustained rate over a short duration of time than do prior art devices. This is possible with the appropriate choice of low molecular weight polymers and water immiscible solvents, and further since the injectable depot gel compositions of the present invention generally have a glass transition temperature, Tg, of less than body temperature of the subject, e.g. 37° C. for humans. Because of the immiscibility of the solvents that are useful in this invention with water, water uptake by the implant is restricted and the pores that do form tend to resemble a closed cell structure without significant numbers of larger pores or pores extending from the surface into the interior of the implant being open at the surface of the implant. Furthermore, the surface pores offer only a limited opportunity for water from body fluids to enter the implant immediately after implantation, thus controlling the burst effect. Since the compositions often will be highly viscous prior to implantation, when the composition is intended for implantation by injection, the viscosity optionally may be modified by the use of viscosity-reducing, miscible solvents or the use of emulsifiers, or by heating to obtain a gel composition having a viscosity or shear resistance low enough to permit passage of the gel composition through a needle.

The limit on the amount of beneficial agent released in the first 24 hours that is either desired or required will depend on circumstances such as the overall duration of the delivery period, the therapeutic window for the beneficial agent, potential adverse consequences due to overdosing, cost of beneficial agent, and the type of effect desired, e.g., systemic or local. Preferably, 40% or less of the beneficial agent will be released in the first 24 hours after implantation, where the percentage is based on the total amount of beneficial agent to be delivered over the duration of the delivery period. Typically, higher percentages of release in the first 24 hours can be tolerated if the duration of the delivery period is relatively short, e.g., a period equal to or less than two weeks, preferably about 10 days or shorter; preferably about 7 days or shorter, more preferably about 3 days to about 7 days, or if the beneficial agent has a wide therapeutic window with little likelihood of side effects, or if the beneficial agent acts locally. In certain embodiments, within 24 hours after implantation the system releases less than or equal to 20% by weight of the amount of beneficial agent to be delivered over the duration of the delivery period, wherein the delivery period is 2 weeks. In additional embodiments, within 24 hours after implantation the system releases less than or equal to 40% by weight of the amount of beneficial agent to be delivered over the duration of the delivery period, wherein the delivery period is one week. In additional embodiments, within 24 hours after implantation the system releases less than or equal to 50% by weight of the amount of beneficial agent to be delivered over the duration of the delivery period, wherein the delivery period is three days.

Depending on the particular solvent or solvent mixture selected, the polymer and beneficial agent, and optionally solubility modulators of the beneficial agent, the compositions of the present invention intended for systemic delivery may provide a gel composition having a burst index of 8 or less, preferably 6 or less, more preferably 4 or less and most preferably 2 or less. Compositions of PLGA weight average molecular weight ranging from about 3000 to about 10,000; preferably from about 3000 to about 9,000; more preferably from about 4000 to about 8,000; and more preferably the low molecular weight polymer has a molecular weight of about 7000, about 6000, about 5000, about 4000 and about 3000 with solvents having a miscibility in water of less than 7% by weight, optionally combined with the other solvents, providing implants intended for systemic delivery of beneficial agent having a burst index of 10 or less, preferably 7 or less, more preferably 5 or less and most preferably 3 or less, are particularly advantageous. The use of solvent mixtures as discussed herein can be particularly advantageous as a means of providing sufficient plasticizing of the polymer to obtain viscous gel formation and at the same time meet the desired burst indices and percentage release objectives of the compositions of the invention.

Compositions intended for local delivery of beneficial agent are forged in the same manner as those intended for systemic use. However, because local delivery of beneficial agent to a subject will not result in detectable plasma levels of beneficial agent, such systems have to be characterized by a percentage of beneficial agent released in a predetermined initial period, rather than a burst index as defined herein. Most typically, that period will be the first 24 hours after implantation and the percentage will be equal to the amount by weight of the beneficial agent released in the period (e.g. 24 hours) divided by the amount by weight of the beneficial agent intended to be delivered in the duration of the delivery period; multiplied by the number 100. Compositions of the present invention will have initial bursts of 40% or less, preferably 30% or less, most preferably 20% or less, for most applications.

In many instances, it may be desirable to reduce the initial burst of beneficial agent during local administration to prevent adverse effects. For example, implants of the invention containing chemotherapeutic agents are suitable for direct injection into tumors. However, many chemotherapeutic agents may exhibit toxic side effects when administered systemically. Consequently, local administration into the tumor may be the treatment method of choice. It is necessary, however, to avoid administration of a large burst of the chemotherapeutic agent if it is possible that such agent would enter the vascular or lymphatic systems where it may exhibit side affects. Accordingly; in such instances the implantable systems of the present invention having limited burst as described herein are advantageous.

The gel formed by mixing the polymer and the solvent typically exhibits a viscosity of from about 100 to about 50,000 poise, preferably from about 500 to about 30,000 poise, more preferably from about 500 to about 10,000 poise measured at a 1.0 sec-1 shear rate and 25° C. using a Haake Rheometer at about 1-2 days after mixing is completed. Mixing the polymer with the solvent can be achieved with conventional low shear equipment such as a Ross double planetary mixer for from about 10 minutes to about 1 hour, although shorter and longer periods may be chosen by one skilled in the art depending on the particular physical characteristics of the composition being prepared. Since the depot gel composition of the invention are administered as an injectable composition, a countervailing consideration when forming depot gel compositions that are viscous gels is that the polymer/solvent/beneficial agent composition have sufficiently low viscosity in order to permit it to be forced through a small diameter, e.g., 18-20 gauge needle. If necessary, adjustment of viscosity of the gel for injection can be accomplished with emulsifying agents or thixotropic agents as described herein. Yet, such compositions should have adequate dimensional stability so as to remain localized and be able to be removed if necessary. The particular gel or gel-like compositions of the present invention satisfy such requirements.

If the polymer composition is to be administered as an injectable gel, the level of polymer dissolution will need to be balanced with the resulting gel viscosity, to permit a reasonable force to dispense the viscous gel from a needle, and the potential burst effect. Highly viscous gels enable the beneficial agent to be delivered without exhibiting a significant burst effect, but may make it difficult to dispense the gel through a needle. In those instances, an emulsifying agent may optionally be added to the composition. Also, since the viscosity may generally be lowered as the temperature of the composition increases, it may be advantageous in certain applications to reduce the viscosity of the gel by heating to provide a more readily injectable composition. The shear thinning characteristics of the depot gel compositions of the present invention allow them to be readily injected into an animal including humans using standard gauge needles without requiring undue dispensing pressure.

When the emulsifying agent is mixed with the viscous gel formed from the polymer and the solvent using conventional static or mechanical mixing devices, such as an orifice mixer, the emulsifying agent forms a separate phase composed of dispersed droplets of microscopic size that typically have an average diameter of less than about 100 microns. The continuous phase is formed of the polymer and the solvent. The particles of the beneficial agent may be dissolved or dispersed in either the continuous phase or the droplet phase. In the resulting thixotropic composition, the droplets of emulsifying agent elongate in the direction of shear and substantially decrease the viscosity of the viscous gel formed from the polymer and the solvent. For instance, with a viscous gel having a viscosity of from about 5,000 to about 50,000 poise measured at 1.0 sec-1 at 25° C., one can obtain a reduction in viscosity to less than 100 poise when emulsified with a 10% ethanol/water solution at 25° C. as determined by Haake Rheometer.

When used, the emulsifying agent typically is present in an amount ranging from about 5 to about 80%, preferably from about 20 to about 60% and often 30 to 50% by weight based on the amount of the injectable depot gel composition, that is the combined amounts of polymer, solvent, emulsifying agent and beneficial agent. Emulsifying agents include, for example, solvents that are not fully miscible with the polymer solvent or solvent mixture. Illustrative emulsifying agents are water, alcohols, polyols, esters, carboxylic acids, ketones, aldehydes and mixtures thereof. Preferred emulsifying agents are alcohols, propylene glycol, ethylene glycol, glycerol, water, and solutions and mixtures thereof. Especially preferred are water, ethanol, and isopropyl alcohol and solutions and mixtures thereof. The type of emulsifying agent affects the size of the dispersed droplets. For instance, ethanol will provide droplets that have average diameters that can be on the order of ten times larger than the droplets obtained with an isotonic saline solution containing 0.9% by weight of sodium chloride at 21° C.

The thixotropic agent, i.e. an agent that imparts thixotropic properties to the polymer gel, is selected from the lower alkanols. Lower alkanol means an alcohol that contains 2-6 carbon atoms and is straight chain or branched chain. Such alcohols may be exemplified by ethanol, isopropanol, and the like. Importantly, such a thixotropic agent is not a polymer solvent. (See e.g., Development of an in situ forming bidegradable poly-lactide-co-glycolide system for controlled release of proteins, Lambert, W. J., and Peck, K. D., Journal of Controlled Release, 33 (1995) 189-195). When used, the thixotropic agent may be present in amounts of 0.01 to 15 weight percent, preferably in amounts of 0.1 to 5 weight percent, and often in amounts of 0.5 to 5 weight percent of the combined weight of the solvent and the thixotropic agent.

It is to be understood that the emulsifying agent and/or the thixotropic agent do not constitute a mere diluent or a polymer-solvent that reduces viscosity by simply decreasing the concentration of the components of the composition. The use of conventional diluents can reduce viscosity, but can also cause the burst effect mentioned previously when the diluted composition is injected. In contrast, the injectable depot composition of the present invention can be formulated to avoid the burst effect by selecting the appropriate low molecular weight polymer, the solvent and emulsifying agent so that once injected into place, the emulsifying agent has little impact on the release properties of the original system.

Although the injectable depot gel composition of the present invention preferably are formed as viscous gels, the means of administration of the implants is not limited to injection, although that mode of delivery may often be preferred. Where the injectable depot gel composition will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

Beneficial Agents:

The beneficial agent can be any physiologically or pharmacologically active substance or substances optionally in combination with pharmaceutically acceptable carriers and additional ingredients such as antioxidants, stabilizing agents, permeation enhancers, etc. that do not substantially adversely affect the advantageous results that can be attained by the present invention. The beneficial agent may be any of the agents which are known to be delivered to the body of a human or an animal and that are preferentially soluble in water rather than in the polymer-dissolving solvent. These agents include drug agents, medicaments, vitamins, nutrients, or the like. Included among the types of agents which meet this description are lower molecular weight compounds, proteins, peptides, genetic material, nutrients, vitamins, food supplements, sex sterilants, fertility inhibitors and fertility promoters.

Drug agents which may be delivered by the present invention include drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, chemotherapeutic agents, immunosuppressive agents, anti-inflammatory agents including anti-inflammatory corticosteroids, antiproliferative agents, antimitotic agents, angiogenic agents, antipsychotic agents, central nervous system (CNS) agents, anticoagulants, fibrinolytic agents, growth factors, antibodies, ocular drugs, and metabolites, analogs (including synthetic and substituted analogs), derivatives (including aggregative conjugates/fusion with other macromolecules and covalent conjugates with unrelated chemical moieties by means known in the art) fragments, and purified, isolated, recombinant and chemically synthesized versions of these species.

Examples of drugs that may be delivered by the composition of the present invention include, but are not limited to, procaine, procaine hydrochloride, tetracaine, tetracaine hydrochloride, cocaine, cocaine hydrochloride, chloroprocaine, chloroprocaine hydrochloride, proparacaine, proparacaine hydrochloride, piperocaine, piperocaine hydrochloride, hexylcaine, hexylcaine hydrochloride, naepaine, naepaine hydrochloride, benzoxinate, benzoxinate hydrochloride, cyclomethylcaine, cyclomethylcaine hydrochloride, cyclomethylcaine sulfate, lidocaine, lidocaine hydrochloride, bupivicaine, bupivicaine hydrochloride, mepivicaine, mepivicaine hydrochloride, prilocaine, prilocaine hydrochloride, dibucaine and dibucaine hydrochloride, etidocaine, benzocaine, propoxycaine, dyclonin, pramoxine, oxybuprocaine, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17α-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat, captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth factors such as epidermal growth factors (EGF), platelet-derived growth factors (PDGF), fibroblast growth factors (FGF), transforming growth factors-α (TGF-α), transforming growth factors-β (TGF-β), erythropoietin (EPO), insulin-like growth factor-I (IGF-I), insulin-like growth factor-II (IGF-II), interleukin-1, interleukin-2, interleukin-6, interleukin-8, tumor necrosis factor-α (TNF-α), tumor necrosis factor-β (TNF-β), Interferon-α (INF-α), Interferon-β (INF-β), Interferon-γ (INF-γ), Interferon-ω (INF-ω), colony stimulating factors (CGF), vascular cell growth factor (VEGF), thrombopoietin (TPO), stromal cell-derived factors (SDF), placenta growth factor (PlGF), hepatocyte growth factor (HGF), granulocyte macrophage colony stimulating factor (GM-CSF), glial-derived neurotropin factor (GDNF), granulocyte colony stimulating factor (G-CSF), ciliary neurotropic factor (CNTF), bone morphogeneic proteins (BMP), coagulation factors, human pancreas hormone releasing factor, analogs and derivatives of these compounds, and pharmaceutically acceptable salts of these compounds, or their analogs or derivatives.

Additional examples of drugs that may be delivered by the composition of the present invention include, but are not limited to, antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin, actinomycin D, daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as $G(GP)II_bIII_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (i.e. estrogen); antipsychotic agents, (such as antipsychotic drugs, neuroleptic drugs, tranquillisers and antipsychotic agents binding to dopamine, histamine, muscarinic cholinergic, adrenergic and serotonin receptors, including but not limited to phenothiazines, thioxanthenes, butyrophenones, dibenzoxazepines, dibenzodiazepines and diphenylbutylpiperidines); central nervous system (CNS) agents; anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcino tone, betamethasone, and dexamethasone), non-steroidal agents (salicylic acid derivatives i.e. aspirin; para-aminophenol derivatives i.e. acetominophen); indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blocker; nitric oxide donors; anti-sense oligionucleotides and combinations thereof; cell cycle inhibitors, mTOR inhibitors, and growth factor signal transduction kinase inhibitors, analogs and derivatives of these compounds, and pharmaceutically acceptable salts of these compounds, or their analogs or derivatives.

In certain preferred embodiments, the beneficial agent includes chemotactic growth factors, proliferative growth factors, stimulatory growth factors, and transformational peptide growth factors including genes, precursors, post-translational-variants, metabolites, binding-proteins, receptors, receptor agonists and antagonists of the following growth factor families: epidermal growth factors (EGFs), platelet-derived growth factor (PDGFs), growth factors (IGFs), fibroblast-growth factors (FGFs), transforming-growth factors (TGFs), interleukins (Ms), colony-stimulating factors (CSFs, MCFs, GCSFs, GMCSFs), Interferons (IFNs), endothelial growth factors (VEGF, EGFs), erythropoietins (EPOs), angiopoietins (ANGs), placenta-derived growth factors (PlGFs), and hypoxia induced transcriptional regulators (HTFs).

The present invention also finds application with chemotherapeutic agents for the local application of such agents to avoid or minimize systemic side effects. Gels of the present invention containing chemotherapeutic agents may be injected directly into the tumor tissue for sustained delivery of the chemotherapeutic agent over time. In some cases, particularly after resection of the tumor, the gel may be implanted directly into the resulting cavity or may be applied to the remaining tissue as a coating. In cases in which the gel is implanted after surgery, it is possible to utilize gels having higher viscosities since they do not have to pass through a small diameter needle. Representative chemotherapeutic agents that may be delivered in accordance with the practice of the present invention include, for example, carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986. The present application has particular utility in the sustained delivery of water soluble chemotherapeutic agents, such as for example cisplatin and carboplatin and the water soluble derivatives of paclitaxel. Those characteristics of the invention that minimize the burst effect are particularly advantageous in the administration of water soluble beneficial agents of all kinds, but particularly those compounds that are clinically useful and effective but may have adverse side effects.

To the extent not mentioned above, the beneficial agents described in aforementioned U.S. Pat. No. 5,242,910 can also be used. One particular advantage of the present invention is that materials, such as proteins, as exemplified by the enzyme lysozyme, and cDNA, and DNA incorporated into vectors both viral and nonviral, which are difficult to microencapsulate or process into microspheres can be incorporated into the compositions of the present invention without the level of degradation caused by exposure to high temperatures and denaturing solvents often present in other processing techniques.

The beneficial agent is preferably incorporated into the viscous gel formed from the polymer and the solvent in the form of particles typically having an average particle size of from about 0.1 to about 250 microns, preferably from about 1 to about 200 microns and often from 30 to 125 microns. For instance, particles having an average particle size of about 5 microns have been produced by spray drying or freeze drying an aqueous mixture containing 50% sucrose and 50% chicken lysozyme (on a dry weight basis) and mixtures of 10-20% hGH and 15-30 mM zinc acetate. Such particles have been used in certain of the examples illustrated in the figures. Conventional Lyophilization processes can also be utilized to form particles of beneficial agents of varying sizes using appropriate freezing and drying cycles.

To form a suspension or dispersion of particles of the beneficial agent in the viscous gel formed from the polymer and the solvent, any conventional low shear device can be used such as a Ross double planetary mixer at ambient conditions. In this manner, efficient distribution of the beneficial agent can be achieved substantially without degrading the beneficial agent.

The beneficial agent is typically dissolved or dispersed in the composition in an amount of from about 0.1% to about 50% by weight, preferably in an amount of from about 1% to about 40%, more preferably in an amount of about 2% to about 30%, and often 2 to 20% by weight of the combined amounts of the polymer, solvent, and beneficial agent. Depending on the amount of beneficial agent present in the composition, one can obtain different release profiles and burst indices. More specifically, for a given polymer and solvent, by adjusting the amounts of these components and the amount of the beneficial agent, one can obtain a release profile that depends more on the degradation of the polymer than the diffusion of the beneficial agent from the composition or vice versa. In this respect, at lower beneficial agent loading rates, one generally obtains a release profile reflecting degradation of the polymer wherein the release rate increases with time. At higher loading rates, one generally obtains a release profile caused by diffusion of the beneficial agent wherein the release rate decreases with time. At intermediate loading rates, one obtains combined release profiles so that if desired, a substantially constant release rate can be attained. In order to minimize burst, loading of beneficial agent on the order of 30% or less by weight of the overall gel composition, i.e., polymer, solvent and beneficial agent, is preferred, and loading of 20% or less is more preferred.

Release rates and loading of beneficial agent will be adjusted to provide for therapeutically-effective delivery of the beneficial agent over the intended sustained delivery period. Preferably, the beneficial agent will be present in the polymer gel at concentrations that are above the saturation concentration of beneficial agent in water to provide a drug reservoir from which the beneficial agent is dispensed. While the release rate of beneficial agent depends on the particular circumstances, such as the beneficial agent to be administered, release rates on the order of from about 0.1 to about 100 micrograms/day, preferably from about 1 to about 10 micrograms per day, for periods of from about 3 to about two weeks can be obtained. Greater amounts may be delivered if delivery is to occur over shorter periods. Generally, higher release rate is possible if a greater burst can be tolerated. In instances where the gel composition is surgically implanted, or used as a "leave behind" depot when surgery to treat the disease state or another condition is concurrently conducted, it is possible to provide higher doses that would normally be administered if the implant was injected. Further, the dose of beneficial agent may be controlled by adjusting the volume of the gel implanted or the injectable gel injected.

FIGS. 1-9 illustrate representative release profiles of various beneficial agents obtained in rats from preferred compositions of this invention. As illustrated in the figures, the injectable depot gel formulations of the invention comprising low molecular weight polymers provide a controlled, sustained release of a beneficial agent over a short duration of time equal to or less than two weeks.

Optional Additional Components:

Other components may be present in the injectable depot gel composition, to the extent they are desired or provide useful properties to the composition, such as polyethylene glycol, hydroscopic agents, stabilizing agents, pore founding agents, and others. When the composition includes a peptide or a protein that is soluble in or unstable in an aqueous environment, it may be highly desirable to include a solubility modulator, that may, for example, be a stabilizing agent, in the composition. Various modulating agents are described in U.S. Pat. Nos. 5,654,010 and 5,656,297 which are incorporated herein by reference. In the case of hGH, for example, it is preferable to include an amount of a salt of a divalent metal, preferably zinc. Examples of such modulators and stabilizing agents, which may form complexes with the beneficial agent or associate to provide the stabilizing or modulated release effect, include metal cations, preferably divalent, present in the composition as magnesium carbonate, zinc carbonate, calcium carbonate, magnesium acetate, magnesium sulfate, zinc acetate, zinc sulfate, zinc chloride, magnesium chloride, magnesium oxide, magnesium hydroxide, other antacids, and the like. The amounts of such agents used will depend on the nature of the complex formed, if any, or the nature of the association between the beneficial agent and the agent. Molar ratios of solubility modulator or stabilizing agent to beneficial agent of about 100:1 to 1:1, preferably 10:1 to 1:1, typically can be utilized.

Pore forming agents include, biocompatible materials that when contacted with body fluids dissolve, disperse or degrade to create pores or channels in the polymer matrix. Typically, organic and non-organic materials that are water soluble such as sugars (e.g., sucrose, dextrose), water soluble salts (e.g., sodium chloride, sodium phosphate, potassium chloride, and sodium carbonate), water soluble solvents such as N-methyl-2-pyrrolidone and polyethylene glycol and water soluble polymers (e.g., carboxmethylcellulose, hydroxypropylcellulose, and the like) can conveniently be used as pore formers. Such materials may be present in amounts varying from about 0.1% to about 100% of the weight of the polymer, but will typically be less than 50% and more typically less than 10-20% of the weight of polymer.

Utility and Administration:

The means of administration of the depot gel compositions is not limited to injection, although that mode of delivery may often be preferred. Where the depot gel composition will be administered as a leave-behind product, it may be formed to fit into a body cavity existing after completion of surgery or it may be applied as a flowable gel by brushing or palleting the gel onto residual tissue or bone. Such applications may permit loading of beneficial agent in the gel above concentrations typically present with injectable compositions.

Compositions of this invention without beneficial agent are useful for wound healing, bone repair and other structural support purposes.

To further understand the various aspects of the present invention, the results set forth in the previously described figures were obtained in accordance with the following examples.

Example 1

Depot Gel Preparation

A gel vehicle for use in an injectable depot of the composition was prepared as follows. A glass vessel was tared on a Mettler P13000 top loader balance. Poly (D,L-lactide-co-glycolide) (PLGA), available as 50:50 DL-PLG with an inherent viscosity of 0.15 (PLGA-BPI, Birmingham Polymers, Inc., Birmingham, Ala.) and 50:50 Resomer® RG502 (PLGA RG 502), was weighed into the glass vessel. The glass vessel containing the polymer was tared and the corresponding solvent was added. Amounts expressed as percentages for various polymer/solvent combinations are set forth in Table 1, below. The polymer/solvent mixture was stirred at 250±50 rpm (MA electric stirrer, IKH-Werke GmbH and Co., Stanfen, Germany) for about 5-10 minutes, resulting in a sticky paste-like substance containing polymer particles. The vessel containing the polymer/solvent mixture was sealed and placed in a temperature controlled incubator equilibrated to 37° C. for 1 to 4 days, with intermittent stirring, depending on solvent and polymer type and solvent and polymer ratios. The polymer/solvent mixture was removed from the incubator when it appeared to be a clear amber homogeneous solution. Thereafter, the mixture was placed in an oven (65 oC) for 30 minutes. It was noted that the PLGA was dissolved in the mixture upon removal from the oven.

Additional depot gel vehicles are prepared with the following solvents or mixtures of solvents: benzyl benzoate ("BB"), benzyl alcohol ("BA"), ethyl benzoate ("EB"), BB/BA, BB/Ethanol, BB/EB and the following polymers: Poly (D,L-lactide-co-glycolide) 50:50 Resomer® RG502, code 0000366, Poly (D,L-lactide-co-glycolide) 50:50 Resomer® RG502H, PLGA-502H, code no. 260187, Poly D,L Lactide (Resomer® R 202, Resomer® R 203); Poly dioxanone (Resomer® X 210) (Boehringer Ingelheim Chemicals, Inc., Petersburg, Va.); DL-lactide/glycolide 100:0 (MEDISORIB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinnati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

Example 2 hGH Particle Preparation

Human growth hormone (hGH) particles (optionally containing zinc acetate) were prepared as follows: hGH solution (5 mg/ml) solution in water (BresaGen Corporation, Adelaide, Australia) was concentrated to 10 mg/mL using a Concentration/Dialysis Selector diafiltering apparatus. The diafiltered hGH solution was washed with 5 times volume of tris or phosphate buffer solution (pH 7.6). Particles of hGH were then formed by spray drying or lyophilization using conventional techniques. Phosphate buffer solutions (5 or 50 mM) containing hGH (5 mg/mL) (and optionally various levels of zinc acetate (0 to 30 mM) when Zn complexed particles were prepared) were spray-dried using a Yamato Mini Spray dryer set at the following parameters:

| Spray Dryer Parameter | Setting |
|---|---|
| Atomizing Air | 2 psi |
| Inlet Temperature | 120° C. |
| Aspirator Dial | 7.5 |
| Solution Pump | 2-4 |
| Main Air Valve | 40-45 psi | hGH particles having a size range between 2-100 microns were obtained. Lyophilized particles were prepared from tris buffer solutions (5 or 50 mM: pH 7.6) containing hGH (5 mg/mL) using a Durastop μP Lyophilizer in accordance with the following freezing and drying cycles;

| Freezing cycle | Ramp down at 2.5 C./min to −30° C. and hold for 30 min |
| | Ramp down at 2.5 C./min to −30° C. and hold for 30 min |
| Drying cycle | Ramp up at 0.5 C./min to 10° C. and hold for 960 min |
| | Ramp up at 0.5 C./min to 20° C. and hold for 480 min |
| | Ramp up at 0.5 C./min to 25° C. and hold for 300 min |
| | Ramp up at 0.5 C./min to 30° C. and hold for 300 min |
| | Ramp up at 0.5 C./min to 5° C. and hold for 5000 min | hGH particles having a size range between 2-100 microns were obtained.

Example 3 hGH-Stearic Acid Particle Preparation

Human growth hormone (hGH) particles were prepared as follows: Lyophilized hGH (3.22 grams, Pharmacia-Upjohn, Stockholm, Sweden) and stearic acid (3.22 grams, 95% pure, Sigma-Aldrich Corporation, St. Louis, Mo.) were blended and ground. The ground material was compressed in a 13 mm round die, with a force of 10,000 pounds for 5 minutes. Compressed tablets were ground and sieved through a 70 mesh screen followed by a 400 mesh screen to obtain particles having a size range between 38-212 microns.

Example 4

Bupivacaine Base Preparation

Bupivacaine hydrochloride (Sigma-Aldrich Corporation, St. Louis, Mo.) was dissolved in de-ionized (DI) water at a concentration of 40 mg/ml (saturation). A calculated amount of sodium hydroxide (1 N solution) was added to the solution and the pH of the final mixtures was adjusted to 10 to precipitate the BP bate. The precipitated product was filtered, and further washed with DI water for at least three times. The precipitated product was dried at approximately 40° C. in vacuum for 24 h.

Example 5

Bupivacaine Particle Preparation

Bupivacaine drug particles using bupivacaine hydrochloride (Sigma-Aldrich Corporation, St. Louis, Mo.) or bupivacaine base prepared according example 4 and hydrochloride salt, were prepared as follows. Bupivicaine was grounded and then sieved to a fixed range using 3" stainless steel sieves. Typical ranges include 25 μm to 38 μm, 38 μm to 63 μm, and 63 μm to 125 μm.

Example 6

Bupivacaine-Stearic Acid Particle Preparation

Bupivacaine particles were prepared as follows: Bupivacaine hydrochloride (100 g, Sigma-Aldrich Corporation, St. Louis, Mo.) was grounded and sieved through 63-125 micron sieves. The bupivacaine particles and stearic acid (100 g, 95% pure, Sigma-Aldrich Corporation, St. Louis, Mo.) were blended and ground. The ground material was compressed in a 13 mm round die, with a force of 5,000 pounds for 5 minutes. Compressed tablets were ground and sieved through a 120 mesh screen followed by a 230 mesh screen to obtain particles having a size range between 63-125 microns.

Example 7

Drug Loading

Particles comprising beneficial agent with or without stearic acid prepared as above were added to a gel vehicle in an amount of 10-30% by weight and blended manually until the dry powder was wetted completely. Then, the milky light yellow particle/gel mixture was thoroughly blended by conventional mixing using a Caframo mechanical stirrer with an attached square-tip metal spatula. Resulting formulations are illustrated in Tables 1, 2 and 3 below.

TABLE 1

| Formulation | PLGA RG502[a] (wt %) | LMW PLGA[b] (wt %) | Benzyl Benzoate (wt %) |
|---|---|---|---|
| 1[c] | 45 | 0 | 45 |
| 2[c] | 0 | 45 | 45 |
| 3[d] | 45 | 0 | 45 |
| 4[d] | 0 | 45 | 45 |

[a]= PLGA RG 502, MW = 16,000.
[b]= Low Molecular Weight (LMW, MW = 8000) PLGA with an ester end group.
[c]= 10% bupivacaine hydrochloride loading.
[d]= 10% bupivacaine base loading.

TABLE 2

| Formulation | PLGA RG502[a] (wt %) | LMW PLGA[e] (wt %) | Benzyl Benzoate (wt %) |
|---|---|---|---|
| 5[f] | 45 | 0 | 45 |
| 6[f] | 0 | 45 | 45 |
| 7[f] | 0 | 63 | 27 |

[a]= PLGA RG 502, MW = 16,000.
[e]= Low Molecular Weight (LMW, MW - 7,000) PLGA with an ester end group.
[f]= 5% hGH loading.

TABLE 3

| Formulation | LMW PLGA[g] (wt %) | LMW PLGAc[h] (wt %) | Benzyl Benzoate (wt %) | Benzyl Alcohol (wt %) |
|---|---|---|---|---|
| 8[i] | 58.5 | 0 | 31.5 | 0 |
| 9[i] | 58.5 | 0 | 0 | 31.5 |
| 10[i] | 67.5 | 0 | 0 | 22.5 |

TABLE 3-continued

| Formulation | LMW PLGA[g] (wt %) | LMW PLGAc[h] (wt %) | Benzyl Benzoate (wt %) | Benzyl Alcohol (wt %) |
|---|---|---|---|---|
| 11[i] | 0 | 67.5 | | 22.5 |
| 12[j] | 0 | 60 | | 20 |

[g]= Low Molecular Weight (LMW, MW = 8,000) PLGA with an ester end group.
[h]= Low Molecular Weight (LMW, MW = 10,000) PLGA with a carboxyl end group.
[i]= 10% bupivacaine hydrochloride loading.
[j]= 10% bupivacaine hydrochloride and 10% SA loading.

A representative number of implantable depots gel compositions were prepared in accordance with the foregoing procedures and tested for in vitro release of beneficial agent as a function of time and also in in vivo studies in rats to determine release of the beneficial agent as determined by blood plasma concentrations of beneficial agent as a function of time.

Example 8

Bupivacaine In Vivo Studies

In vivo studies in rats (4 or 5 per group) were performed following an open protocol to determine plasma levels of bupivacaine upon systemic administration of bupivicaine via the implant systems of this invention. Depot gel bupivacaine formulations were loaded into customized 0.5 cc disposable syringes, Disposable 18 gauge needles were attached to the syringes and were heated to 37° C. using a circulator bath. Depot gel bupivacaine formulations were injected into rats and blood was drawn at specified time intervals (1 hour, 4 hours and on days 1, 2, 5, 7, 9, 14, 21 and 28) and analyzed for bupivacaine using LC/MS.

Figure 2:
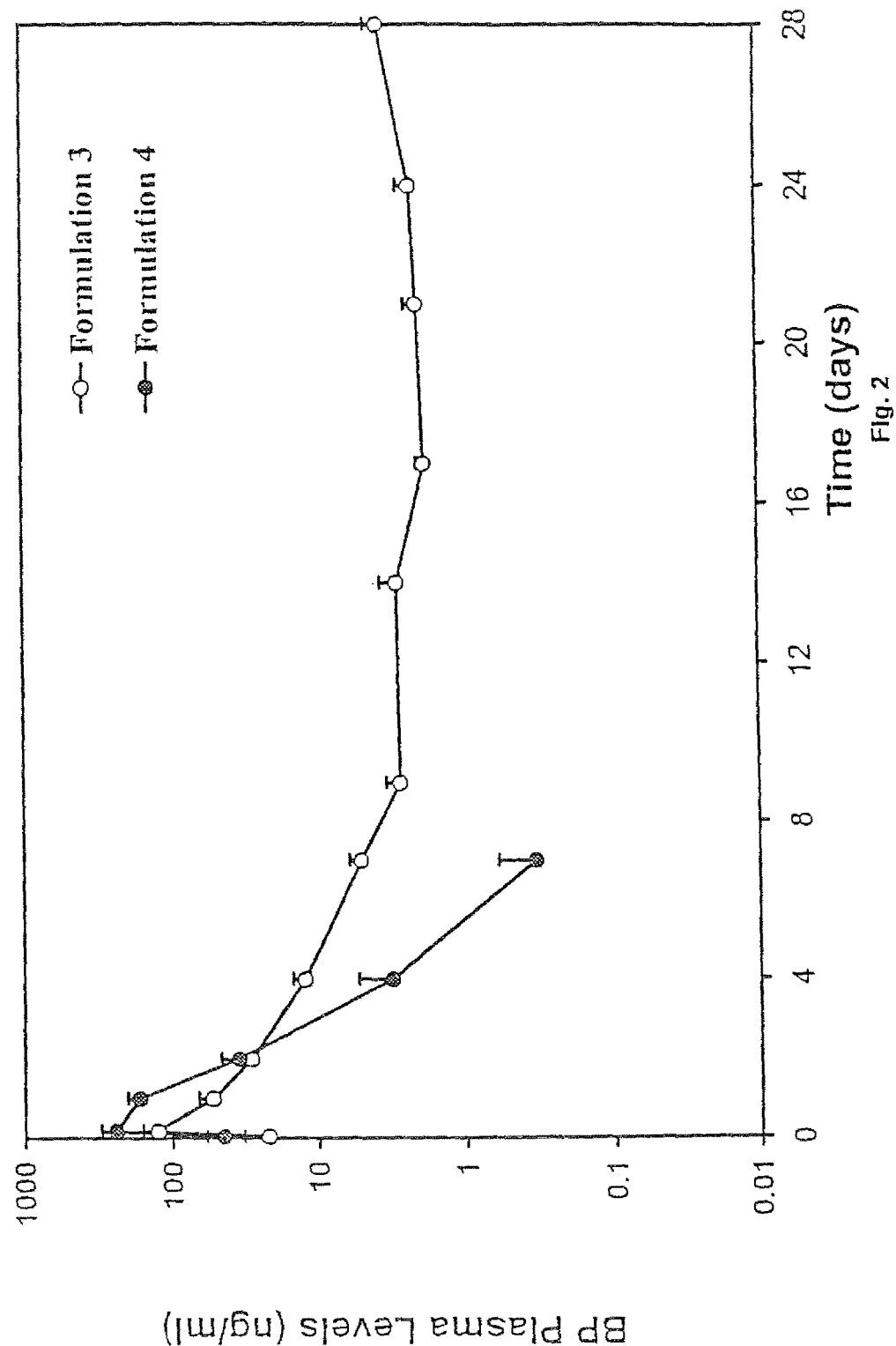
FIG. 2 is a graph illustrating the in vivo release profile of bupivacaine base obtained from depot formulations of the present invention (formulations 3-4).
Figure 3:
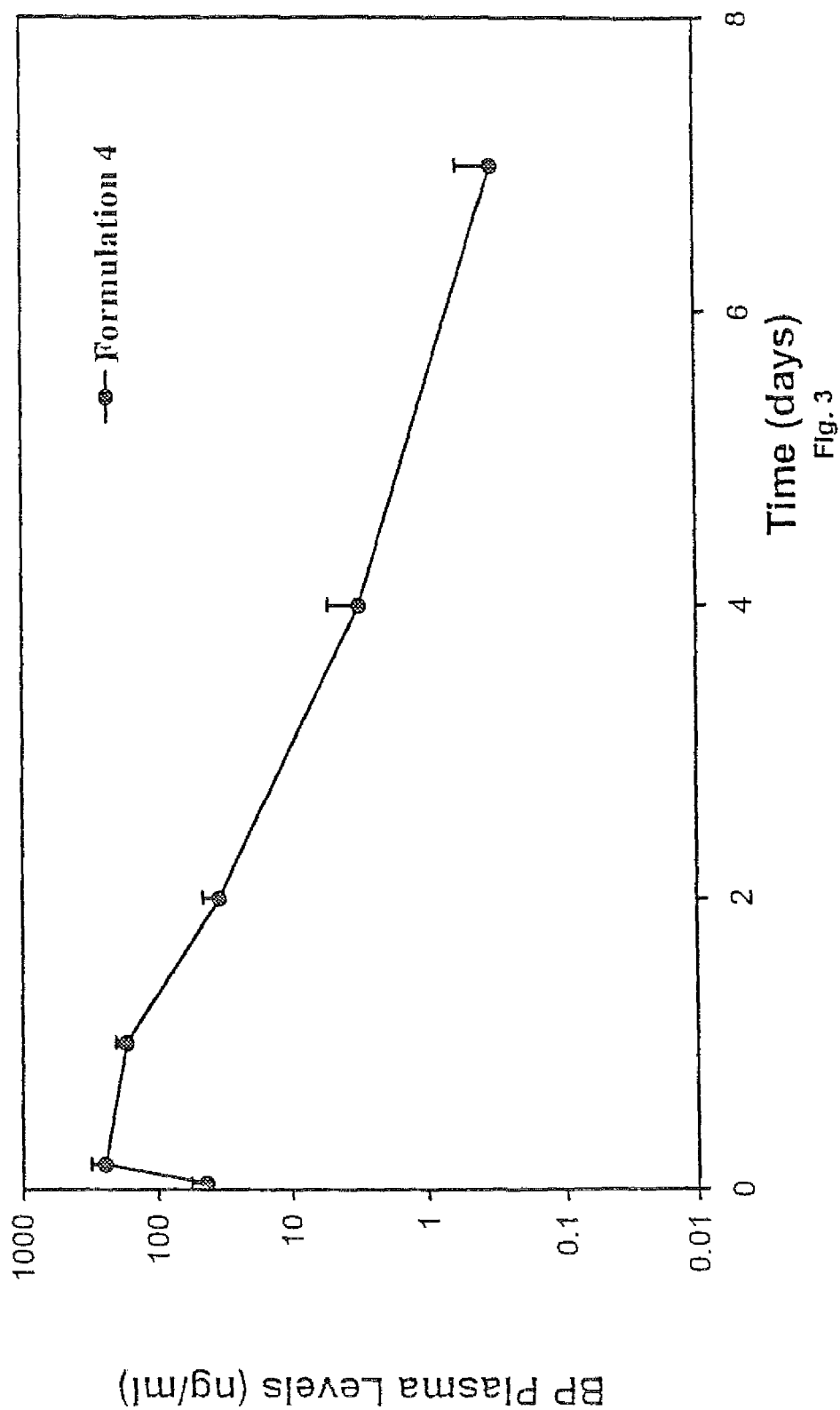
FIG. 3 is a graph illustrating the in vivo release profile of bupivacaine base obtained from a depot formulation of the present invention (formulation 4).

FIGS. 1, 2 and 3 illustrate representative in vivo release profiles of bupivacaine hydrochloride and bupivacaine base obtained in rats from various depot formulation, including those of the present invention. The in vivo release profile of the depot formulations with low molecular weight PLGA (formulations 2 and 4 in FIGS. 1, 2 and 3) exhibited short release duration for approximately 7 days, comparable to the control formulations (with higher molecular weight PLGA). Thus, the injectable depot gel formulations of the invention comprising low molecular weight polymers provide a controlled, sustained release of a beneficial agent over a short duration of time equal to or less than two weeks.

Example 9 hGH In Vivo Studies

In vivo hGH studies in rats were performed following an open protocol to determine serum levels of hGH upon systemic administration of hGH via the injectable depot gel compositions of this invention. Depot gel hGH formulations were loaded into customized 0.5 cc disposable syringes. Disposable 16 gauge needles were attached to the syringes and were heated to 37° C. using a circulator bath. Depot gel hGH formulations were injected into immunosuppressed rats and blood was drawn at specified time intervals. All serum samples were stored at 4° C. prior to analysis. Samples were analyzed for intact hGH content using a radio immuno assay (RIA).

Figure 4:
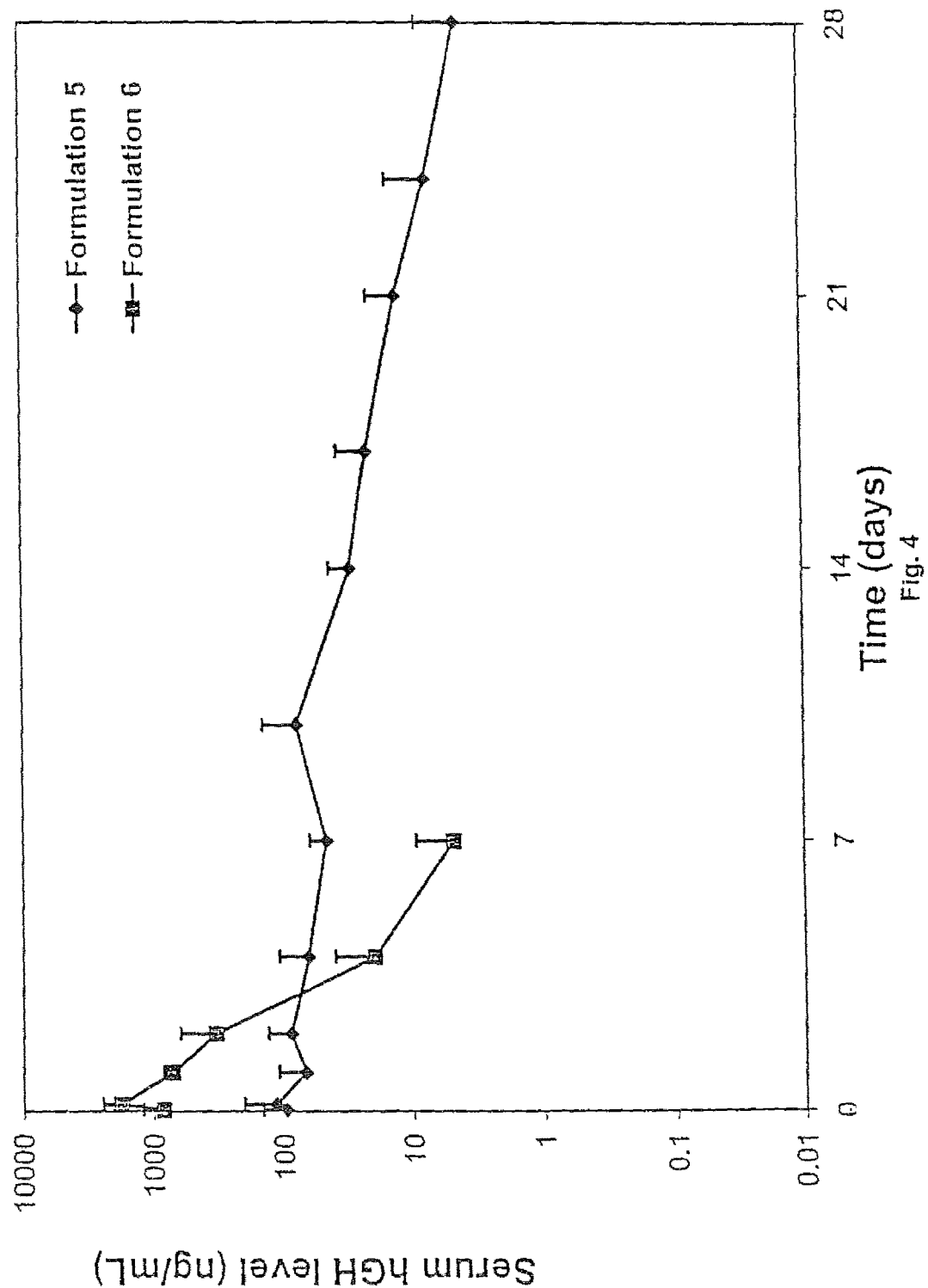
FIG. 4 is a graph illustrating the in vivo release profile of human growth hormone (hGH) obtained from depot formulations of the present invention (formulations 5-6).
Figure 5:
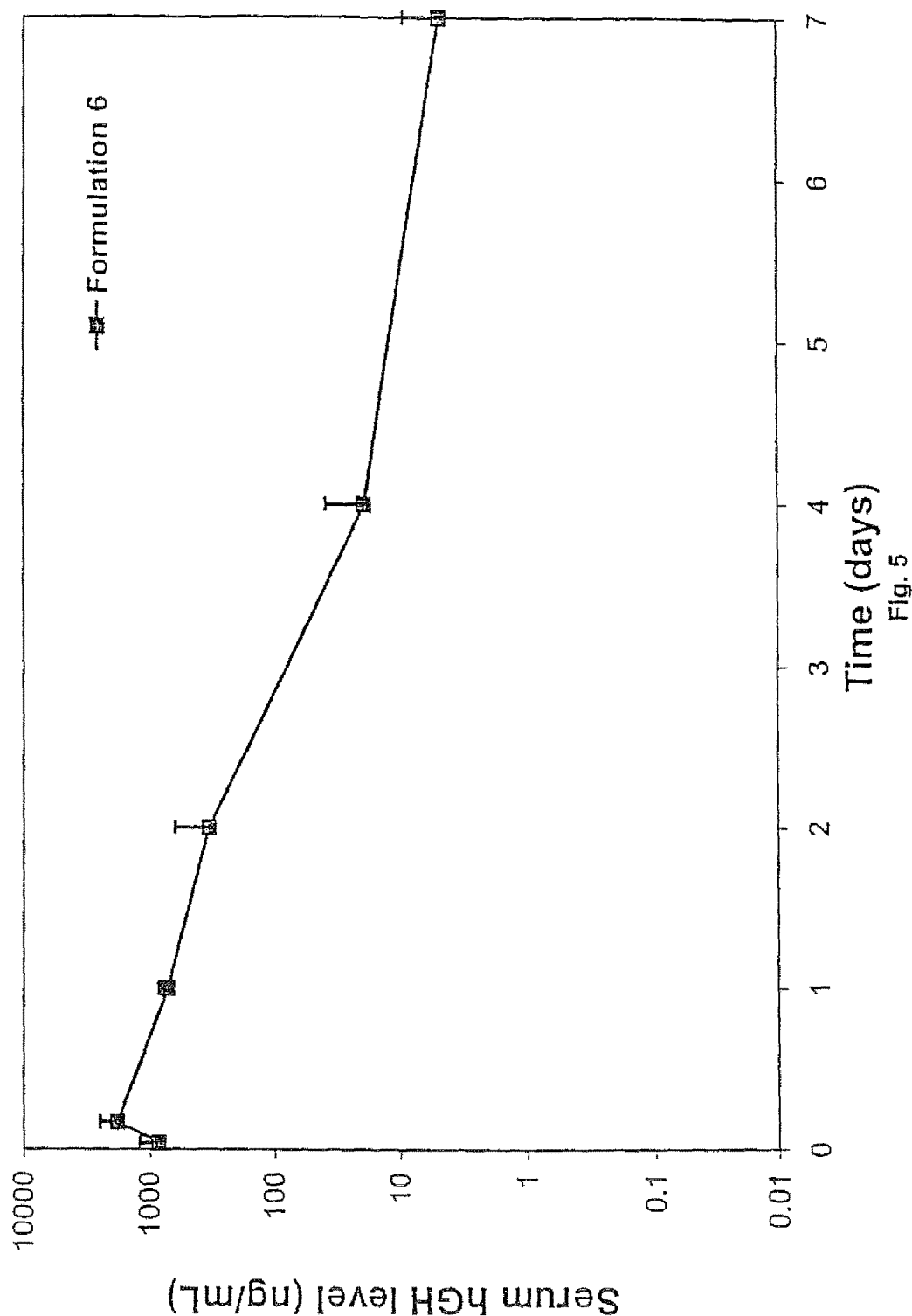
FIG. 5 is a graph illustrating the in vivo release profile of hGH obtained from a depot formulation of the present invention (formulation 6).
Figure 6:
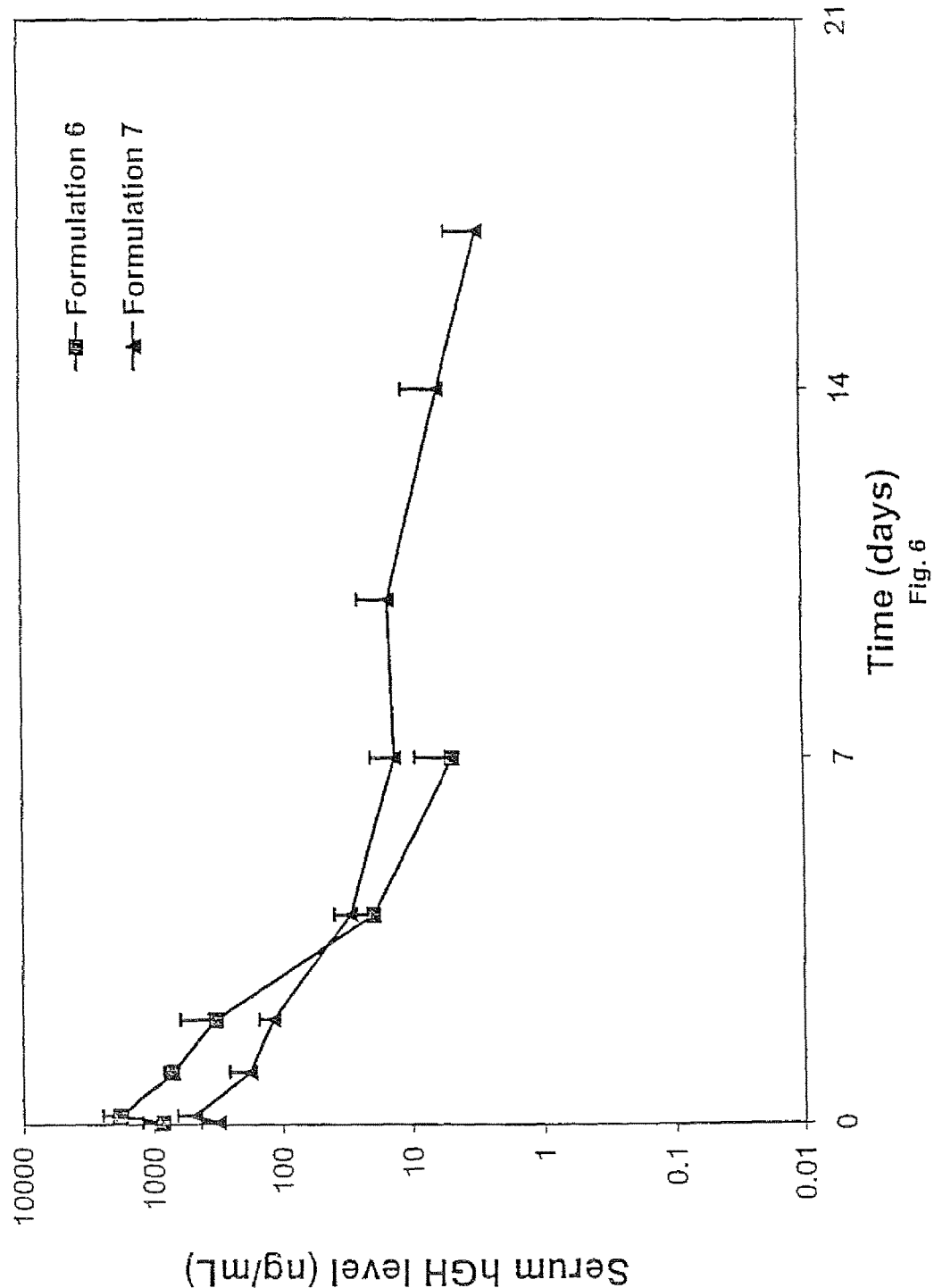
FIG. 6 is a graph illustrating the in vivo release profile of hGH obtained from depot formulations of the present invention (formulations 6-7)

FIGS. 4, 5 and 6 illustrate representative in vivo release profiles of human growth hormone ("hGH") obtained in rats from various depot formulation, including those of the present invention. The in vivo release profile of the depot formulations with low molecular weight PLGA (formulations 6 and 7 in FIGS. 4, 5 and 6) exhibited short release duration for approximately 7-14 days, comparable to the control formulations (with higher molecular weight PLGA). Thus, the injectable depot gel formulations of the invention comprising low molecular weight polymers provide a controlled, sustained release of a beneficial agent over a short duration of time equal to or less than two weeks.

Example 10

In Vivo Studies on Bupivacaine Depot Formulation

As illustrated in Table 3, various depot formulations can be made from the low molecular weight PLGA with either an ester end group or a carboxyl end group using different solvents such as benzyl benzoate (BB), benzyl alcohol (BA), ethyl benzoate (EB), mixtures of BB/Ethanol, BB/BA, BB/EB etc., with varying polymer/solvent ratios. The drug particles can be made either with or without hydrophobic excipients such as stearic acid (SA).

Figure 7:
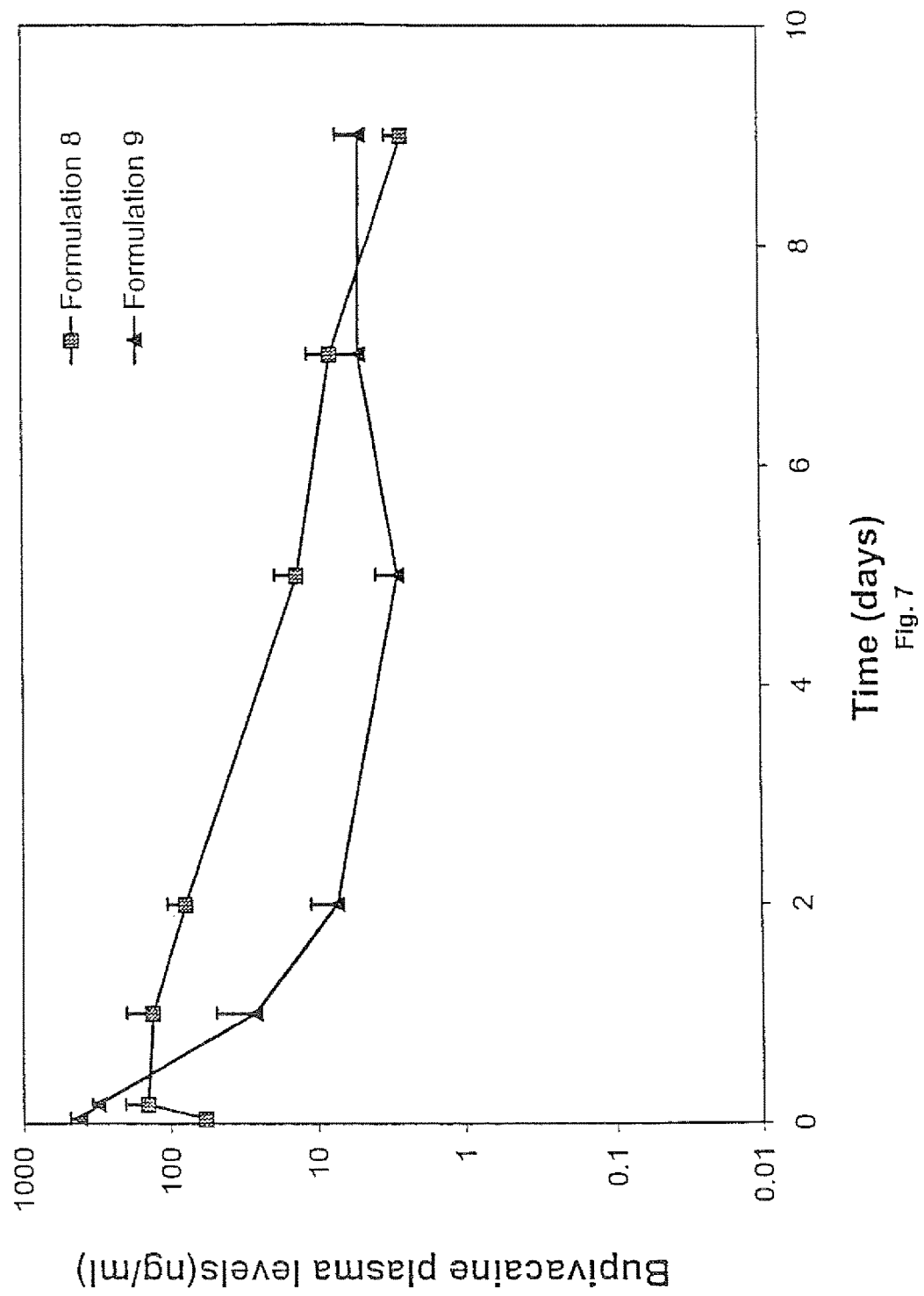
FIG. 7 is a graph illustrating the in vivo release profile of bupivacaine obtained from depot formulations of the present invention (formulations 8-9).
Figure 8:
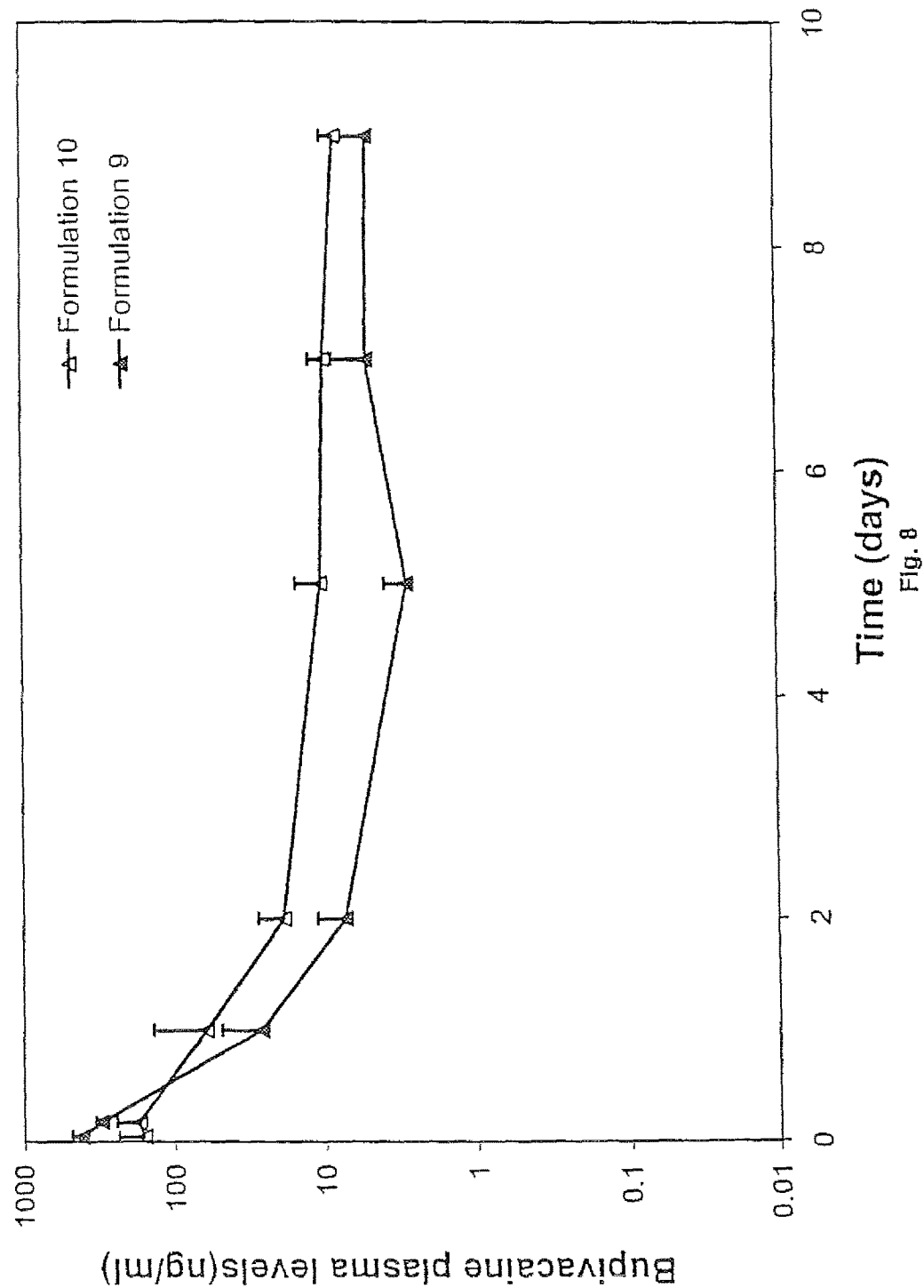
FIG. 8 is a graph illustrating the in vivo release profile of bupivacaine obtained from depot formulations of the present invention (formulations 9-10).
Figure 9:
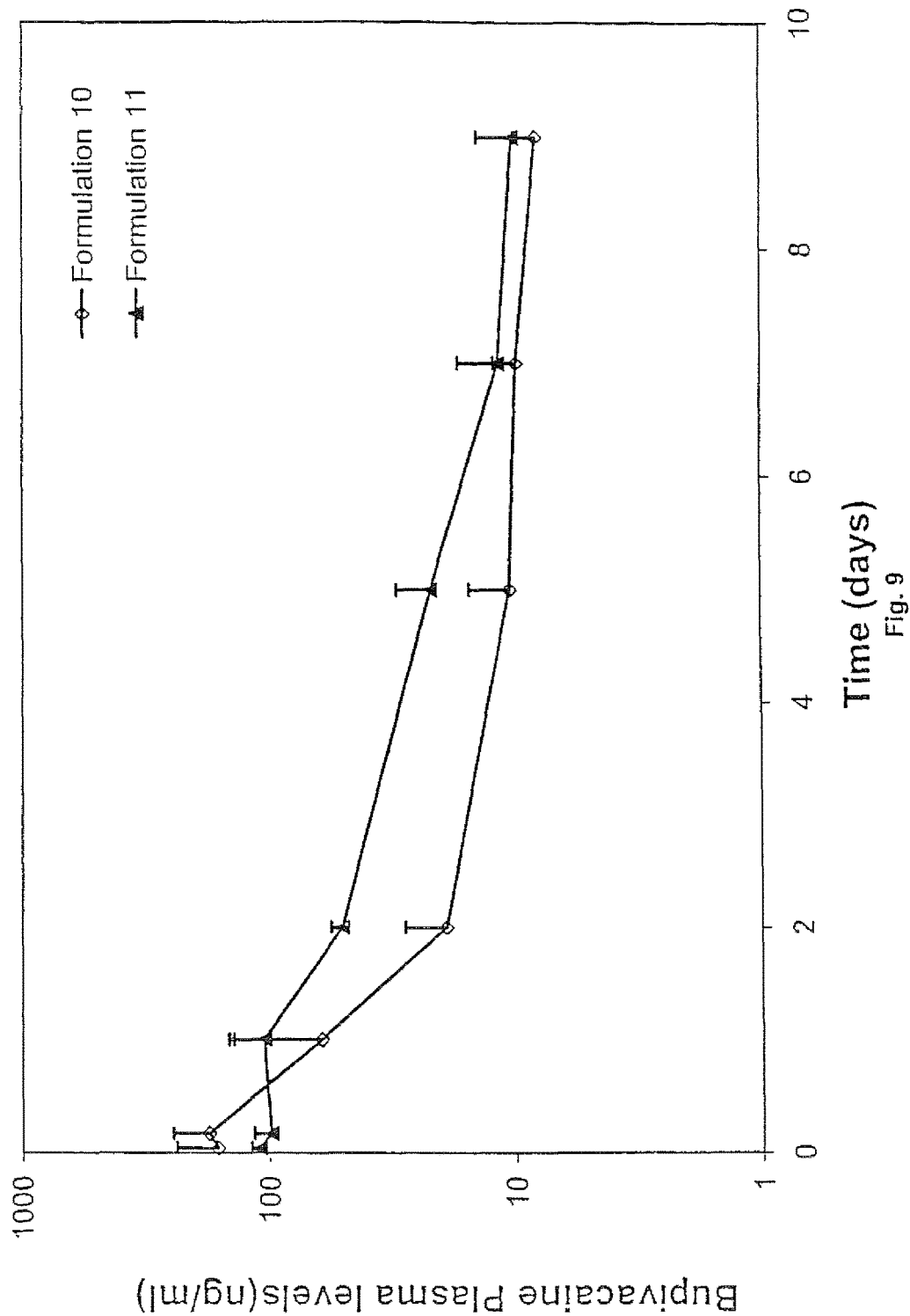
FIG. 9 is a graph illustrating the in vivo release profile of bupivacaine obtained from depot formulations of the present invention (formulations 10-11).
Figure 10:
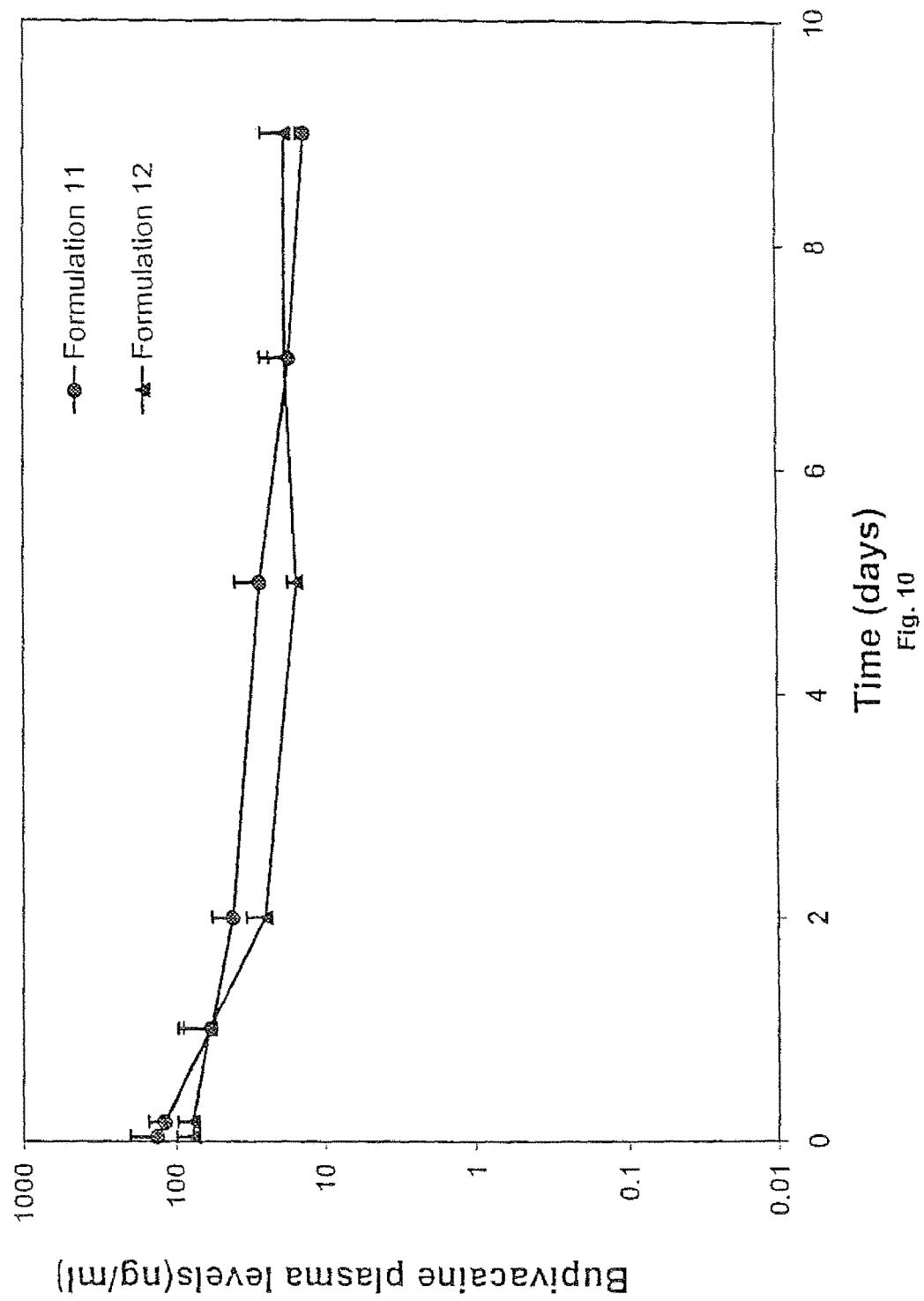
FIG. 10 is a graph illustrating the in vivo release profile of bupivacaine obtained from depot formulations of the present invention (formulations 11-12).

FIG. 7 illustrates representative in vivo release profiles of bupivacaine obtained in rats from depot formulations made of low molecular weight PLGA in either BB or BA. FIG. 8 illustrates representative in vivo release profiles of bupivacaine obtained in rats from depot formulations made of low molecular weight PLGA in BA with various polymer/solvent ratios. FIG. 9 illustrates representative in vivo release profiles of bupivacaine obtained in rats from depot formulations made of low molecular weight PLGA in BA with different end groups. FIG. 10 illustrates representative in vivo release profiles of bupivacaine obtained in rats from depot formulations made of low molecular weight PLGA in BA with the drug particles formulated either with or without SA.

As illustrated in this example, by using low molecular weight PLGA either end-capped with an ester or carboxyl group, the short duration release of active agent from depot can be achieved. The formulations can be made in various solvents or solvent mixtures with various polymer/solvent ratios. The release profiles of the active agent from the depots can be varied accordingly.

Example 11

Differential Scanning Calorimeter (DSC) Measurements on PLGA Polymers

The glass transition temperature of various low molecular PLGA polymers used in the present invention was determined using a differential scanning calorimeter (DSC) (Perkin Elmer Pyris 1, Shelton, Conn.). The DSC sample pan was tarred on a Mettler P13000 top loader balance. At least 20 mg of polymer sample was placed in the pan. The weight of the sample was recorded. The DSC pan cover was positioned on to the pan and a presser was used to seal the pan. The temperature was scanned in 10° C. increments from −50° C. to 90° C.

Figure 11:
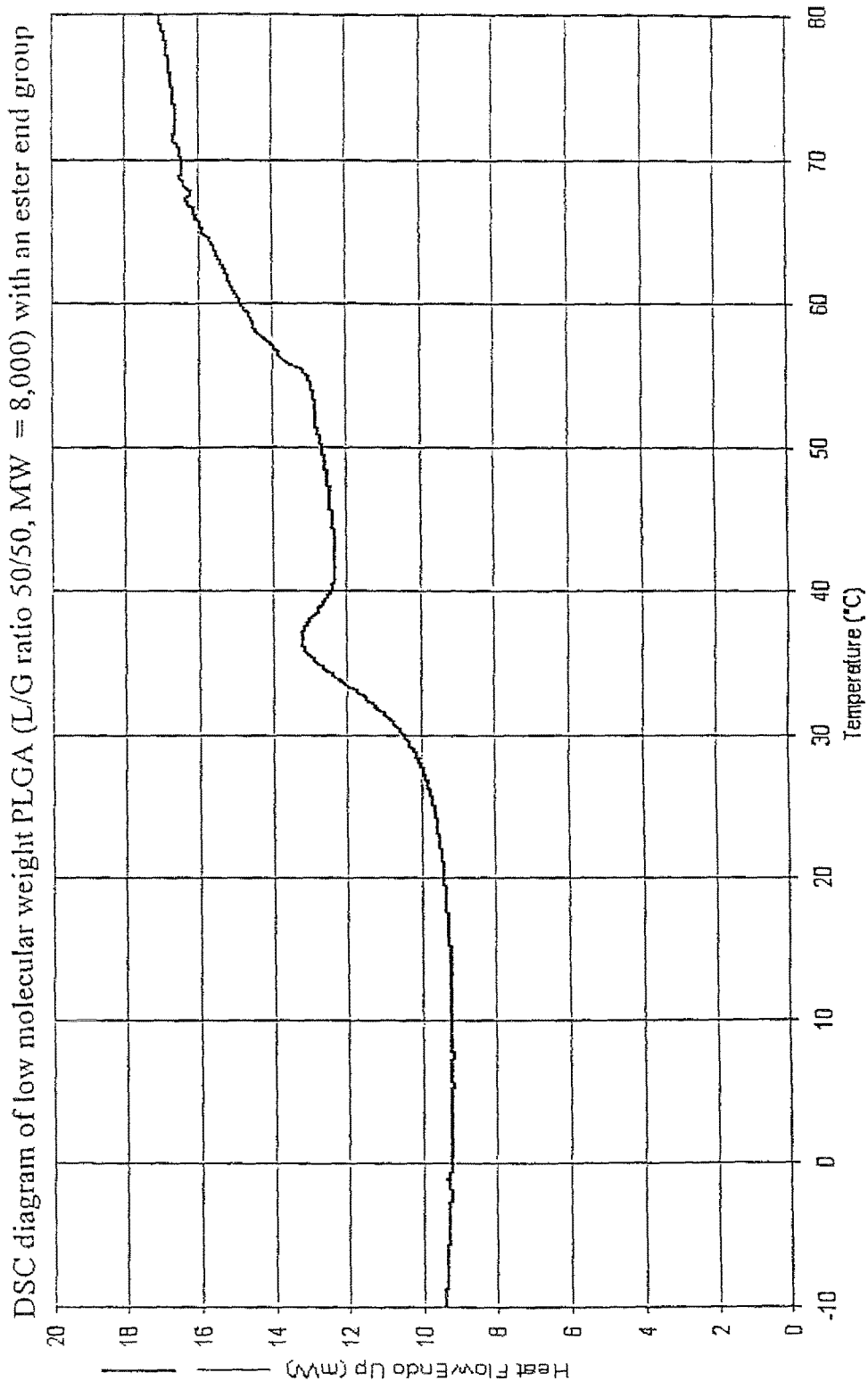
FIG. 11 is a DSC diagram of the low molecular weight PLGA with an ester end group used to make various formulations of the present invention (formulations 2, 4, 6, 7, 11, and 12).
Figure 12:
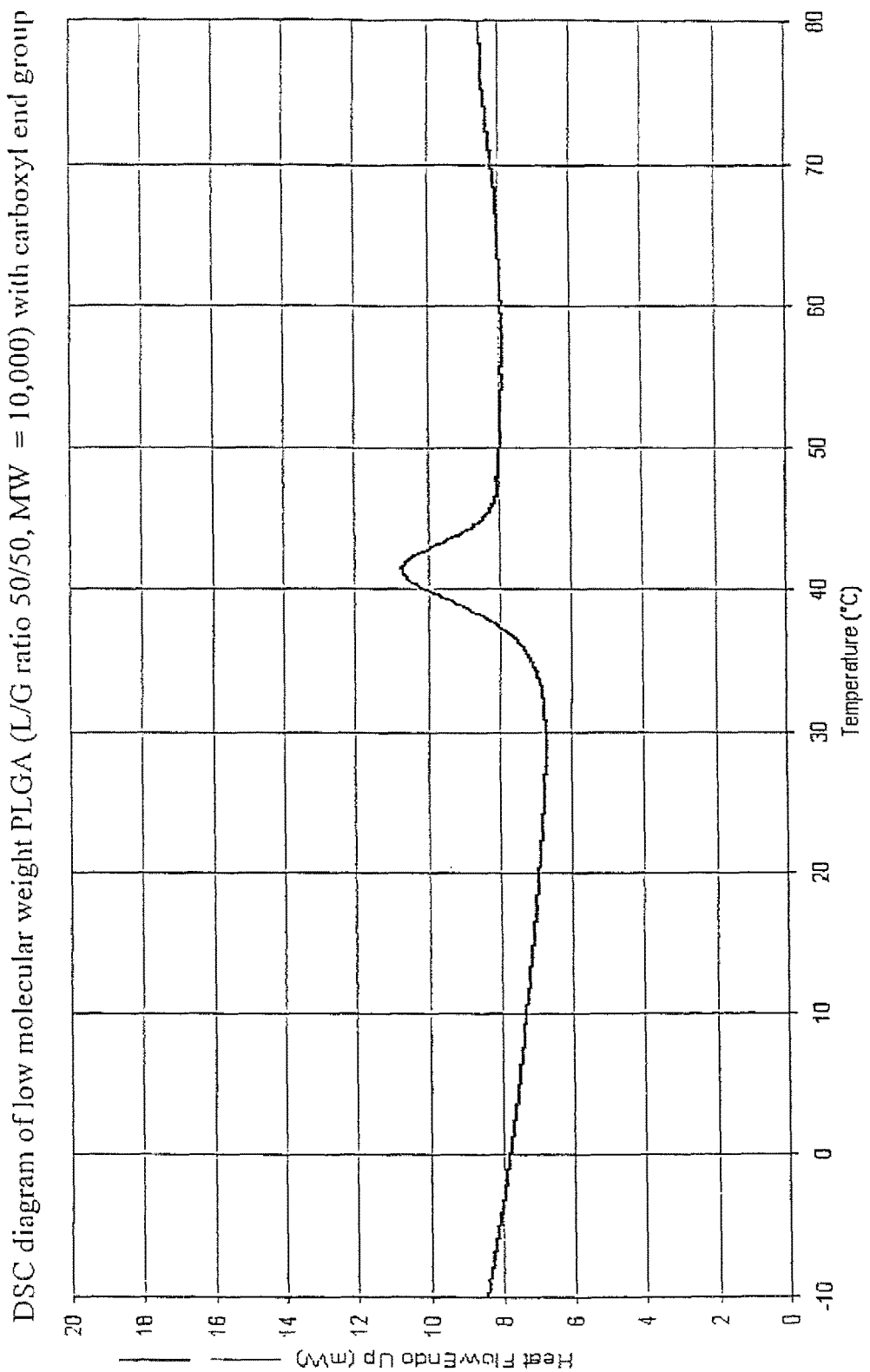
FIG. 12 is a DSC diagram of the low molecular weight PLGA with a carboxyl end group used to make a various formulations of the present invention (formulations 8, 9, and 10).

FIGS. 11 and 12 illustrate the differences in the DSC diagrams of low molecular weight PLGA used in the formulations presented in this invention end-capped with either an ester group or the carboxyl terminated. These data demonstrate that the low molecular weight PLGA polymers used in this invention have a glass transition temperatures ("Tg") above 30° C.

Example 12

In Vitro Degradation of PLGA Polymers

The degradation profiles of low molecular weight PLGA polymers used in the present invention were performed in vitro at 37° C. in PBS buffer to determine the mass loss rate of the PLGA polymer as a function of time. Each of the copolymers comprised one sample set. Approximately 25 discs (100±5 mg each) were pressed using a 13 mm stainless steel die. The sample was pressed with 10 tons of force for approximately 10 minutes using the Carver Press. The discs were kept in a glass vial in a vacuum oven at ambient temperature and 25 mm Hg until ready for use in the degradation bath. This procedure was repeated for each polymer tested. Phosphate buffered saline (PBS) solution (50 mM, pH 7.4) with sodium azide (0.1N) was prepared. One sample disc was weighed into the tarred vial and recorded as initial weight ($M_{initial}$). PBS (10 mL) was pipetted into each vial. The vial was capped securely and placed in a 37° C. shaking water bath. The buffer was changed twice a week, prior to which the pH of the solution was recorded. At pre-designated time points, the samples were removed from the buffer bath, rinsed with de-ionized Milli-Q water, dried superficially, and weighed. The sample weight was recorded as wet weight ($M_{wet}$). The sample was placed in a 10 mL lyophilization vial and placed in a freezer (−20° C.) prior to lyophilization. After lyophilization, the samples were weighed again and recorded as dry weight ($M_{lyophilized}$). The percent mass loss was defined as $\{(M_{lyophilized}-M_{initial})/M_{initial}\}\times 100\%$.

Figure 13:
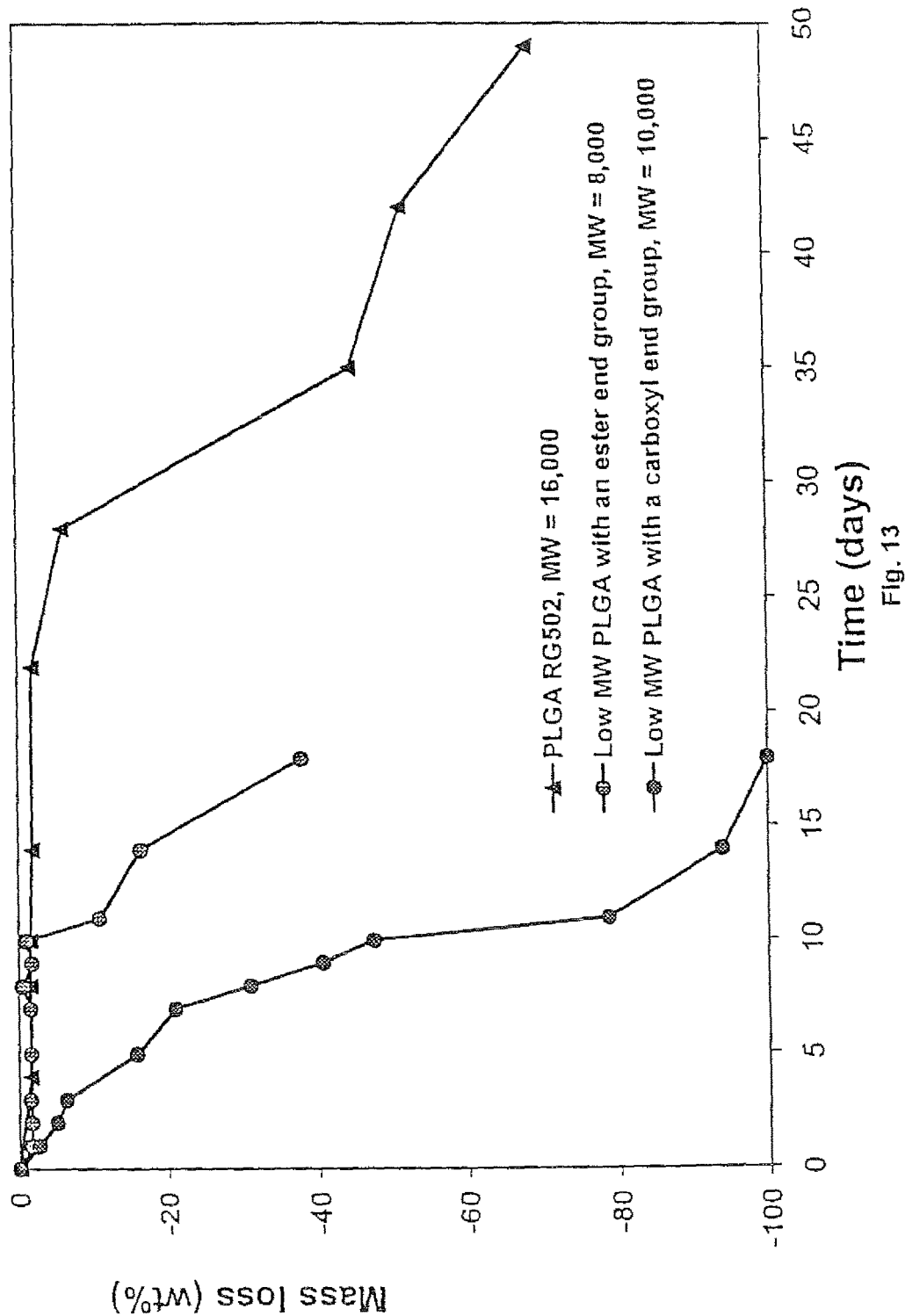
FIG. 13 is a graph illustrating the in vitro degradation profile of PLGA polymers of varying molecular weights with different end groups.

FIG. 13 illustrates the mass loss profiles of the three PLGAs used in the formulations described above. From this it can be seen that each of the three polymers used has significantly different degradation rates. The low molecular weight PLGA with either an ester end group or carboxyl end group have a significantly faster degradation rate than the one with higher molecular weight. This represents more favorable towards short duration depots which prefers the polymer degrades as soon as the active agents are released from the depot. In accordance with various aspects of the present invention, one or more significant advantages can be obtained. More specifically, using simple processing steps, one can obtain a depot gel composition that can be injected into place in an animal without surgery using a low dispensing force through standard needles. Once in place, the composition will quickly return to its original viscosity and may exhibit rapid hardening so as to substantially avoid a burst effect and provide the desired beneficial agent release profile. Furthermore, once the beneficial agent has been fully administered, there is no need to remove the composition since it is fully biodegradable. As a still further advantage, the present invention avoids the use of microparticle or microcapsulation techniques which can degrade certain beneficial agents, like peptide and nucleic acid-based drugs and which microparticles and microcapsules may be difficult to remove from the environment of use. Since the viscous gel is formed without the need for water, temperature extremes, or other solvents, suspended particles of beneficial agent remain dry and in their original configuration, which contributes to the stability of thereof. Further, since a mass is formed, the injectable depot gel composition may be retrieved from the environment of use if desired.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention.

We claim:

1. A method of administering bupivacaine base or pharmaceutically acceptable salt thereof, comprising administering to a subject a composition comprising:
   a polyorthoester having a weight average molecular weight ranging from 3000 to 10,000;
   triacetin; and
   bupivacaine base or pharmaceutically acceptable salt thereof in an amount ranging from 1 wt % to 20 wt % of the composition,
   wherein the weight ratio of polyorthoester to triacetin ranges from 40:60 to 75:25.

2. The method of claim 1, wherein the bupivacaine base or pharmaceutically acceptable salt thereof consists of bupivacaine base.

3. The method of claim 1, wherein the polyorthoester has a weight average molecular weight ranging from 4000 to 8000.

4. The method of claim 2, wherein the polyorthoester has a weight average molecular weight ranging from 4000 to 8000.

5. The method of claim 1, wherein the bupivacaine base or pharmaceutically acceptable salt thereof is present in an amount ranging from 2 wt % to 20 wt % of the composition.

6. The method of claim 2, wherein the bupivacaine base is present in an amount ranging from 2 wt % to 20 wt % of the composition.

7. The method of claim 3, wherein the bupivacaine base or pharmaceutically acceptable salt thereof is present in an amount ranging from 2 wt % to 20 wt % of the composition.

8. The method of claim 4, wherein the bupivacaine base is present in an amount ranging from 2 wt % to 20 wt % of the composition.

9. The method of claim 1, wherein the weight ratio of polyorthoester to triacetin ranges from 50:50 to 75:25.

10. The method of claim 2, wherein the weight ratio of polyorthoester to triacetin ranges from 50:50 to 75:25.

11. The method of claim 3, wherein the weight ratio of polyorthoester to triacetin ranges from 50:50 to 75:25.

12. The method of claim 4, wherein the weight ratio of polyorthoester to triacetin ranges from 50:50 to 75:25.

13. The method of claim 5, wherein the weight ratio of polyorthoester to triacetin ranges from 50:50 to 75:25.

14. The method of claim 6, wherein the weight ratio of polyorthoester to triacetin ranges from 50:50 to 75:25.

15. The method of claim 7, wherein the weight ratio of polyorthoester to triacetin ranges from 50:50 to 75:25.

16. The method of claim 8, wherein the weight ratio of polyorthoester to triacetin ranges from 50:50 to 75:25.

17. The method of claim 1, wherein the bupivacaine base or pharmaceutically acceptable salt thereof is released from the composition in a controlled manner over a duration equal to or less than two weeks.

18. The method of claim 1, wherein the bupivacaine base or pharmaceutically acceptable salt thereof is released from the composition in a controlled manner over a duration ranging from 24 hours to 2 weeks.

19. The method of claim 1, wherein the bupivacaine base or pharmaceutically acceptable salt thereof is released from the composition in a controlled manner over a duration ranging from 24 hours to 10 days.

20. The method of claim 1, wherein the bupivacaine base or pharmaceutically acceptable salt thereof is released from the composition in a controlled manner over a duration ranging from 24 hours to 7 days.

21. The method of claim 1, wherein the administering comprises locally administering.

22. A method of administering bupivacaine base or pharmaceutically acceptable salt thereof, comprising administering to a subject a composition comprising:
- a polyorthoester having a weight average molecular weight ranging from 3000 to 10,000;
- a solvent comprising triacetin and at least one of dimethyl sulfoxide and N-methyl-2-pyrrolidone; and
- bupivacaine base or pharmaceutically acceptable salt thereof in an amount ranging from 1 wt % to 20 wt % of the composition,
- wherein the weight ratio of polyorthoester to solvent ranges from 40:60 to 75:25.

23. The method of claim 22, wherein the bupivacaine base or pharmaceutically acceptable salt thereof comprises bupivacaine base.

24. The method of claim 22, wherein the polyorthoester has a weight average molecular weight ranging from 4000 to 8000.

25. The method of claim 23, wherein the polyorthoester has a weight average molecular weight ranging from 4000 to 8000.

26. The method of claim 22, wherein the bupivacaine base or pharmaceutically acceptable salt thereof is present in an amount ranging from 2 wt % to 20 wt % of the composition.

27. The method of claim 23, wherein the bupivacaine base or pharmaceutically acceptable salt thereof is present in an amount ranging from 2 wt % to 20 wt % of the composition.

28. The method of claim 24, wherein the bupivacaine base or pharmaceutically acceptable salt thereof is present in an amount ranging from 2 wt % to 20 wt % of the composition.

29. The method of claim 25, wherein the bupivacaine base or pharmaceutically acceptable salt thereof is present in an amount ranging from 2 wt % to 20 wt % of the composition.

30. The method of claim 22, wherein the weight ratio of polyorthoester to solvent ranges from 50:50 to 75:25.

31. The method of claim 23, wherein the weight ratio of polyorthoester to solvent ranges from 50:50 to 75:25.

32. The method of claim 24, wherein the weight ratio of polyorthoester to solvent ranges from 50:50 to 75:25.

33. The method of claim 25, wherein the weight ratio of polyorthoester to solvent ranges from 50:50 to 75:25.

34. The method of claim 26, wherein the weight ratio of polyorthoester to solvent ranges from 50:50 to 75:25.

35. The method of claim 27, wherein the weight ratio of polyorthoester to solvent ranges from 50:50 to 75:25.

36. The method of claim 28, wherein the weight ratio of polyorthoester to solvent ranges from 50:50 to 75:25.

37. The method of claim 29, wherein the weight ratio of polyorthoester to solvent ranges from 50:50 to 75:25.

38. The method of claim 22, wherein the bupivacaine base or pharmaceutically acceptable salt thereof is released from the composition in a controlled manner over a duration equal to or less than two weeks.

39. The method of claim 22, wherein the bupivacaine base or pharmaceutically acceptable salt thereof is released from the composition in a controlled manner over a duration ranging from 24 hours to 2 weeks.

40. The method of claim 22, wherein the bupivacaine base or pharmaceutically acceptable salt thereof is released from the composition in a controlled manner over a duration ranging from 24 hours to 10 days.

41. The method of claim 22, wherein the bupivacaine base or pharmaceutically acceptable salt thereof is released from the composition in a controlled manner over a duration ranging from 24 hours to 7 days.

42. The method of claim 22, wherein the administering comprises locally administering.

* * * * *